(12) United States Patent
Mangione et al.

(10) Patent No.: US 10,667,921 B2
(45) Date of Patent: *Jun. 2, 2020

(54) MEDICAL IMPLANT

(71) Applicant: ET MEDICAL TECHNOLOGIES, LLC, North Massapequa, NY (US)

(72) Inventors: Richard Mangione, North Massapequa, NY (US); Tony Ray Meyer, Jr., North Massapequa, NY (US); Einat Lampert, Merrick, NY (US)

(73) Assignee: ET MEDICAL TECHNOLOGIES, LLC, North Massapequa, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,418

(22) Filed: Aug. 14, 2017

(65) Prior Publication Data

US 2018/0185160 A1 Jul. 5, 2018

Related U.S. Application Data

(63) Continuation of application No. 15/162,267, filed on May 23, 2016, now Pat. No. 9,730,800, which is a (Continued)

(51) Int. Cl.
*A61F 2/02* (2006.01)
*A61F 2/42* (2006.01)
(Continued)

(52) U.S. Cl.
CPC .......... *A61F 2/4225* (2013.01); *A61B 17/562* (2013.01); *A61F 2/0059* (2013.01); *A61F 2/3872* (2013.01); *A61F 13/067* (2013.01); *A61F 2002/4233* (2013.01); *A61F 2250/0003* (2013.01); *A61F 2250/0034* (2013.01)

(58) Field of Classification Search
CPC ...... A61F 2/3872; A61F 2/30756; A61F 2/52; A61F 2002/30581; A61F 2002/4223; A61F 13/067; A61F 5/14; A61F 5/0111; A61F 5/0127; A43B 17/026; A43B 17/18
See application file for complete search history.

(56) References Cited

U.S. PATENT DOCUMENTS

| 4,211,236 A | 7/1980 | Krinsky |
| 4,592,755 A | 6/1986 | Penton |

(Continued)

FOREIGN PATENT DOCUMENTS

CN 101827563 A 9/2010

OTHER PUBLICATIONS

STIC search results.
(Continued)

*Primary Examiner* — Dinah Baria
(74) *Attorney, Agent, or Firm* — Knobbe, Martens, Olson & Bear, LLP

(57) ABSTRACT

An implant can be used for the treatment of fat pad atrophy. The implant can be installed in the ball of the foot, the heel of the foot, the hands, or other areas. The implant can supplement or replace a patient's fat pads. In some instances, the implant can include an implant pad having a non-permeable external lining and an internal cavity enclosed by the external lining. The internal cavity can include a filler material. The implant can include features that resist rupture and/or migration.

13 Claims, 14 Drawing Sheets

Related U.S. Application Data continuation of application No. 15/161,082, filed on May 20, 2016, now abandoned.

(60) Provisional application No. 62/165,395, filed on May 22, 2015.

(51) Int. Cl.
*A61F 2/00* (2006.01)
*A61B 17/56* (2006.01)
*A61F 13/06* (2006.01)
*A61F 2/38* (2006.01)

(56) References Cited

U.S. PATENT DOCUMENTS

| | | |
|---|---|---|
| 4,707,872 A | 11/1987 | Hessel |
| 4,932,969 A | 6/1990 | Frey et al. |
| 5,171,281 A | 12/1992 | Parsons et al. |
| 6,110,210 A | 8/2000 | Norton et al. |
| 7,670,378 B2 | 3/2010 | Bloemer et al. |
| 7,892,264 B2 | 2/2011 | Sanders et al. |
| 7,942,930 B2 | 5/2011 | Agerup et al. |
| 8,691,259 B2 | 4/2014 | Bowman et al. |
| 9,314,339 B2 | 4/2016 | Mansmann |
| 2007/0142920 A1 | 6/2007 | Niemi |
| 2008/0200989 A1 | 8/2008 | Cachia |
| 2010/0249946 A1 | 9/2010 | Lesh et al. |
| 2011/0224796 A1 | 9/2011 | Weiland et al. |
| 2011/0276136 A1 | 11/2011 | Koole et al. |
| 2012/0207792 A1 | 8/2012 | Boutros |
| 2013/0030529 A1 | 1/2013 | Hunt |
| 2014/0257481 A1 | 9/2014 | Brooks et al. |

OTHER PUBLICATIONS

Vella, Joseph et al. "Expert Insights on Therapies for Plantar Fat Pad Atrophy," Podiatry Today, Jun. 1, 2015, vol. 28, No. 6.
International Search Report and Written Opinion in International Application No. PCT/US2016/033635, dated Aug. 9, 2016.

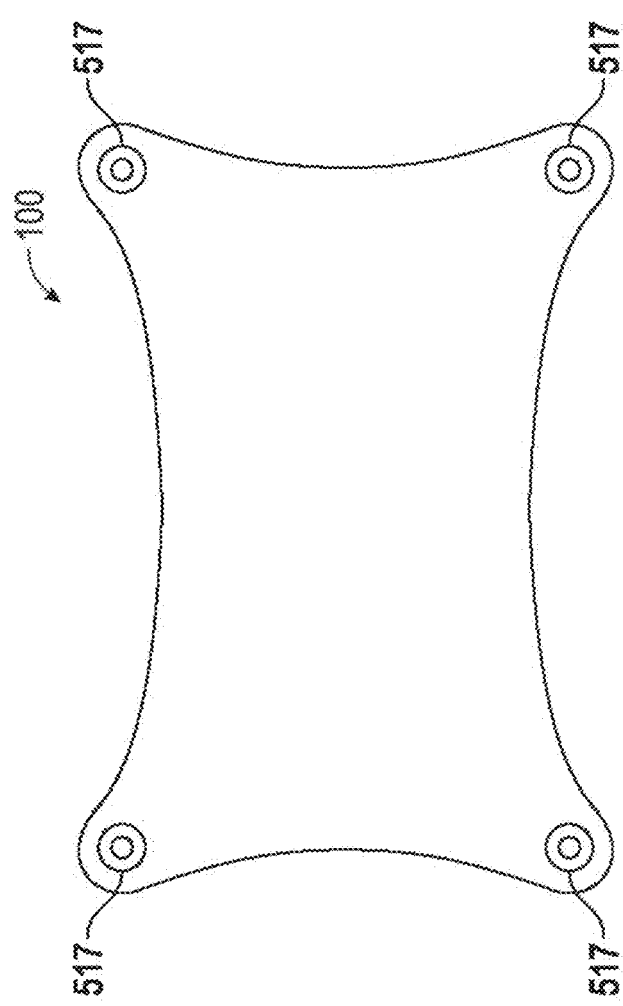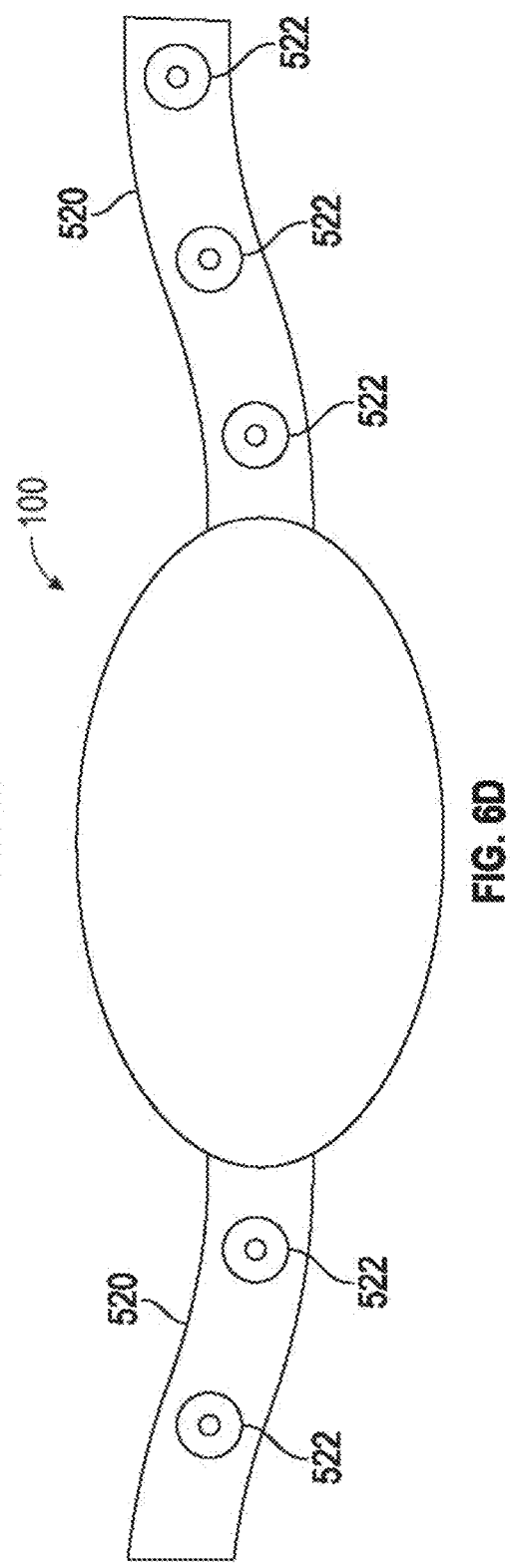
FIG. 6C
FIG. 6D

US 10,667,921 B2

MEDICAL IMPLANT

CROSS-REFERENCE TO RELATED APPLICATIONS

This application is a continuation of U.S. patent application Ser. No. 15/162,267, filed on May 23, 2016, which is a continuation of U.S. patent application Ser. No. 15/161,082, filed on May 20, 2016, which claims priority to U.S. Provisional Application No. 62/165,395, filed on May 22, 2015, each of which is incorporated herein by reference in its entirety.

BACKGROUND

The human body contains fat pads in various locations. The fat pads can provide cushioning and protection. For example, fat pads in the hands and feet provide cushioning and protection for the bones, tendons, ligaments, tissues, blood vessels, nerves, etc., in the hands and feet that can commonly experience high forces. In the foot, plantar fat pads are on the bottom of each foot, both below the ball and heel of the foot. The plantar fat pads are composed of flexible chambers of fatty tissue. These plantar fat pads protect the feet by absorbing the impact, forces, and pressures that are involved in nearly every type of activity, including, for example, walking, running, playing sports, and even simply standing still.

The fat pads in the body can be subject to deterioration or atrophy. Plantar fat pad atrophy is the gradual loss of the plantar fat pad. The loss of the plantar fat pad can occur due to genetics, foot trauma, or natural aging. Additionally, poorly designed footwear and/or diabetes can be contributing factors to plantar fat pad atrophy. The loss of one's plantar fat pad can pose serious issues for one's health and well-being. Significant plantar fat pad atrophy can lead to pain and discomfort, nerve entrapment, difficulty with walking and daily activity, as well as stress and compound fractures, among other injurious effects. As the foot is required to support up to seven times a person's body weight, the damage posed by plantar fat pad deterioration can be a significant health risk.

SUMMARY

An implant can be used for the treatment of fat pad atrophy. The implant can be surgically installed in or around a region of fat pad atrophy to supplement and/or replace a patient's fat pads. In some instances, the implant absorbs forces to replace or supplement the cushioning provided by a patient's fat pads. In some instances, the implant radiates, dissipates, and/or spreads forces. The implant can be installed in the ball of the foot, the heel of the foot, the hands, or other areas.

In some instances, the implant can include an implant pad having a non-permeable external lining and an internal cavity enclosed by the external lining. The internal cavity can include a filler material. In some instances, the implant can include a plurality of conjoined implant pads. In some instances, the implant can include a solid implant pad.

The implant can include features that resist rupture and/or migration. For example, the external lining can include one or more layers of material having different resonant frequencies. In some instances, the internal cavity of the implant can include internal walls defining one or more chambers. In some instances, the internal cavity can include a flexible matrix of porous walls. In some instances, an exterior surface of the implant can include a texture that reduces, limits, or prevents migration of the implant. In some instances, one or more anchors or anchor points extend from the implant to secure the implant and reduce, limit, or prevent migration. The anchors or anchor points can be attached by sutures, mechanical fasteners, adhesives, and/or other methods to anatomical features surrounding the implant, such as, bones (for example, the metatarsals or calcaneus) or soft tissue (for example, the plantar fascia).

These and other features of the implants, as well as methods for its use, are described in greater detail below.

BRIEF DESCRIPTION OF THE DRAWINGS

The features and advantages of the implants of this disclosure, as well as the methods for their use described herein, will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale. Furthermore, it is intended that anyone or any combination of the described embodiments can be used alone or in combination with the other described embodiments.

FIG. 6C is a diagram illustrative of an embodiment of an implant that includes grommets in the corners to secure the implant.

FIG. 6D is a diagram illustrative of an embodiment of an implant that includes bands that can be used to secure the implant.

DETAILED DESCRIPTION

Figure 1A:
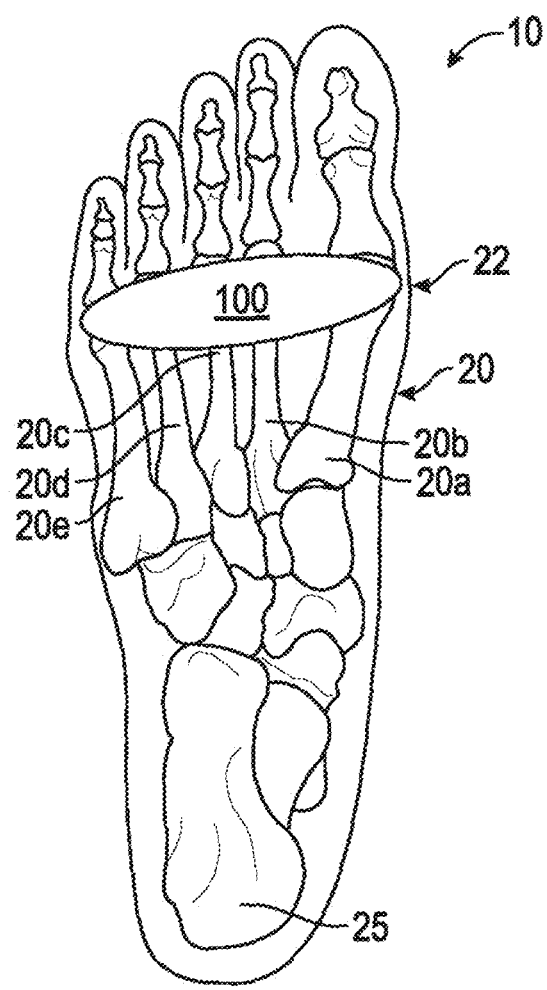
FIGS. 1A and 1B are diagrams illustrative of plantar and medial views, respectively, of a foot including an implant.

This disclosure generally relates to implants, which in some cases can be used to treat fat pad atrophy. The implants can be surgically installed in the hand, foot, or other locations to replace or supplement a patient's fat pad, such as a plantar fat pad. In some cases, the implant can be used to replace or supplement other soft tissue, such as cartilage. As will be described in greater detail throughout, in some embodiments, an implant can be configured to withstand the high and highly variable forces and the wide range of movements and motions experienced at the surgical location (for example, within the foot, hand, or elsewhere) without rupturing or migrating from the implant's installed position. Although various aspects of the implant and methods for treatment are described below with regard to examples and embodiments, including those illustrated in the figures, one skilled in the art will appreciate that the disclosed examples and embodiments should not be construed as limiting. For example, the features of these examples can be modified, duplicated, removed, and/or combined with features described with regards to other examples. Further, while this disclosure may describe examples of using the implant in the treatment of plantar fat pad atrophy in the ball of the foot, it is not limited to this application. The implant can be used (or modified for use) in other locations (for example, the heel of the foot, the arch of the foot, the hand, or other locations) and for other applications.

The implant and methods described herein can provide several advantages over existing treatments for fat pad atrophy. For example, in some embodiments, the implant can provide a permanent or long lasting solution. In some embodiments, the implant of the present disclosure can last for upwards of ten years, or longer. In addition, with some embodiments of the implant, the risk of non-compliance or misuse by the patient is reduced. Further, in some embodiments, the implant can reduce or eliminate the risk of further fat pad deterioration. In addition, since the implant can push up the metatarsal head, it can, in some embodiments, reduce strain in the foot and lower the risk of hammertoe development.

There are additional benefits to the implant and methods described herein as well. For example, the implants of the present disclosure may not have a real aesthetic impact on the foot, allowing patients to continue their daily lives with little to no disruption or alteration. The implants and methods described herein can also help with Charcot foot, which is an issue with the arch of the foot, as well as plantar fat pad atrophy in the heel of the foot.

The implant and methods will now be described in reference to several embodiments illustrated in the figures. These embodiments are provided by way of examples only, and the features of these embodiments can be modified, duplicated, removed, and/or combined with features described in relation to other examples or in ways apparent to those skilled in the art.

Example Implant

Figure 1B:
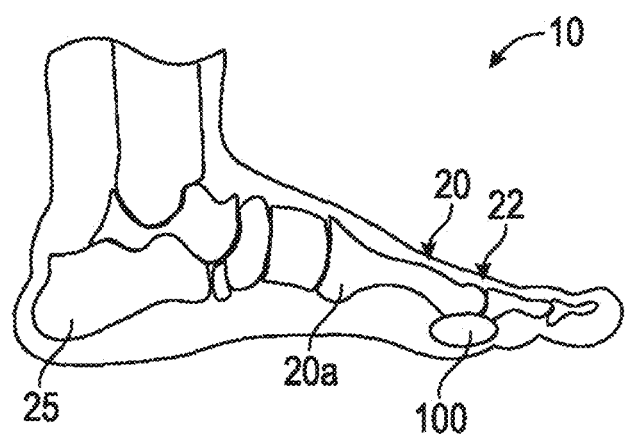

FIGS. 1A and 1B are diagrams illustrative of plantar and medial views, respectively, of a foot 10 including an embodiment of an implant 100 for the treatment of plantar fat pad atrophy. The bones of the foot 10, including the metatarsals 20, are also depicted. In the illustrated embodiment, the implant 100 is positioned below and/or between the heads 22 of the metatarsals 20. As shown in the plantar view of FIG. 1A, the implant 100 extends substantially across the width of the foot 10, substantially below and/or between the heads 22 of the first through fifth metatarsals 20*a*-20*e*. The shape and position of the implant 100 shown in FIGS. 1A and 1B is provided by way of example and is not intended to be limiting. The implant 100 can include one or more of the features described throughout this application in any combination. Although the implant 100 is shown installed in the foot 10 for the treatment of plantar fat pad atrophy, it will be appreciated that the implant 100 can also be installed in other locations in the body.

The implant 100 can be configured to serve as a replacement or a supplement for one or more plantar fat pads of a patient. The plantar fad pads are generally positioned below the heads 22 of the metatarsals 20 and the calcaneus 25 of the foot 10. The plantar fat pads are composed of micro-chambers that contain fatty tissue. The micro-chambers are formed by walls of elastin that are flexible and pliable. The fat filled micro-chambers stretch and rebound to help absorb and dissipate the forces and pressures endured by the feet during activity. The plantar fat pads, however, can deteriorate or atrophy.

To replace or supplement atrophied plantar fat pads as a treatment for plantar fat pad atrophy, the implant 100 can be surgically installed in the foot 10 in the region of the plantar fat pad (or a portion thereof). For example, the implant can be installed as shown in FIGS. 1A and 1B below the heads 22 of the metatarsals 20 for treatment for plantar fat pad atrophy in the ball of the foot 10. Additionally or alternatively, the implant 100 can be surgically installed in the foot below the calcaneus 25 as a treatment for plantar fat pad atrophy in the heel of the foot 10. In some embodiments, the implant 100 can be surgically installed in other locations, for example, in the arch of the foot, in the hand, or in locations of other fat pads in the body.

In the illustrated embodiment of FIGS. 1A and 1B, the implant 100 includes a single implant pad that extends substantially across the width of the foot 10 below and/or between the heads 22 of the first through fifth metatarsals 20*a*-20*e*. However, it will be understood that the implant 100 can be formed using various widths, sizes, and/or numbers of implant pads as desired. For example, in some embodiments, the implant 100 can be sized to replace or supplement a fat pad for a single metatarsal, a subset of metatarsals, or all of the metatarsals as desired. In some embodiments, multiple implants 100 can be installed, with each implant 100 positioned proximate to the fat pads of one or more of the metatarsal heads and/or replacing or supplementing a fat pad for a particular metatarsal. Thus, in some embodiments, the implant 100 (or one or more implants 100) can be installed in regions of the foot 10 experiencing plantar fat pad atrophy to provide a targeted treatment.

As several examples (among others), the implant 100 can be used to treat fat pad atrophy below the head 22 of the second metatarsal 20b, on the medial and/or lateral sides of the bottom of foot 10, below the heads 22 of the first metatarsal 20a and the fifth metatarsal 20e, below the heads 22 of the third and/or fourth metatarsals 20c, 20d, or across the width of the foot below the first through fifth metatarsal 20a-20e.

Figure 2:
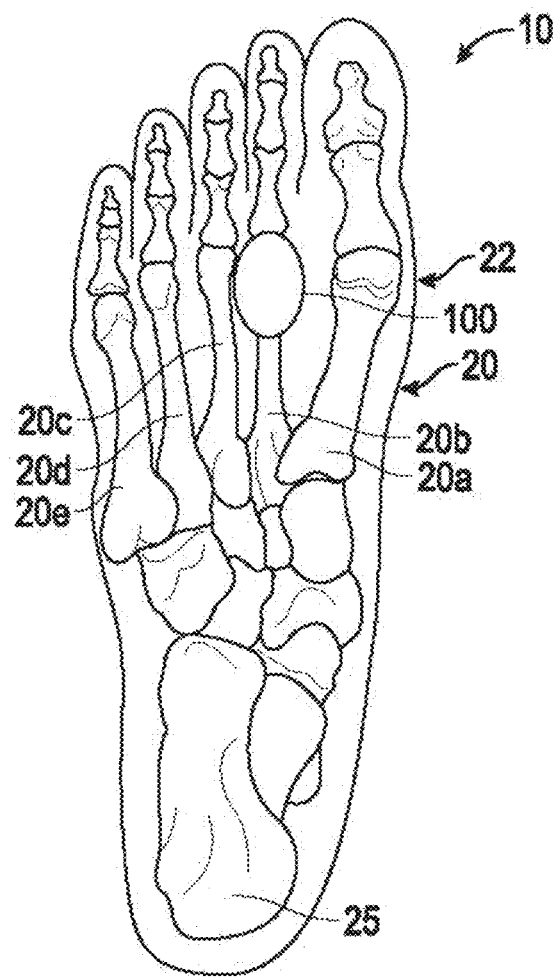
FIG. 2 is a diagram illustrative of a plantar view of a foot including an embodiment of an implant positioned below the second metatarsal head.

As noted previously, the implant 100 can be used for targeted treatment in the area or areas of plantar fat pad atrophy (for example, only below one or more of the metatarsal heads, as shown in FIG. 2 where the implant 100 is positioned below the head 22 of the second metatarsal 20b), or the implant 100 can be used to replace or supplement the plantar fat pads across the entire width of the foot (in other words, below the first through fifth metatarsal heads, as shown in FIG. 1A).

In some embodiments, the width of the implant 100 (measured as the implant's widest dimension across the width of the foot 10) can be approximately 15 cm or less, approximately 12 cm or less, approximately 10 cm or less, or approximately 8 cm or less. In some embodiments, the width of the implant 100 is between approximately 8 cm and approximately 12 cm. In some embodiments, length of the implant 100 (measured as the implant's longest dimension along the length of the foot 10) can be approximately 4 cm or less, approximately 2 cm or less, or approximately 1 cm or less. In some embodiments, the length of the implant 100 can be between approximately 1.5 cm and approximately 2.5 cm. In some embodiments, the thickness of the implant 100 can be approximately 4 cm or less, approximately 2 cm or less, or approximately 1 cm or less. In some embodiments, the thickness of the implant 100 can be between approximately 0.5 mm and approximately 2 cm. In some embodiments, the thickness of the implant 100 is smaller than the length and/or width of the implant 100. For example, in some embodiments, the thickness of the implant 100 can be between 1% and 25% of the length and/or width of the implant 100. In certain cases, the thickness can be 50% of the length and/or width of the implant 100. Furthermore, it will be understood that other lengths, widths, and thicknesses for the implant 100 can be used.

In some embodiments, the width and thickness of the implant 100 are substantially equal. In some embodiments, the length and thickness of the implant 100 are substantially equal. In some embodiments, the length and the width of the implant 100 are substantially equal. In some embodiments, the dimensions (length, width, and/or thickness) of the implant 100 are chosen to correspond to the area of plantar fat pad atrophy to be treated. In some embodiments, the thickness of the implant 100 can be substantially constant across the length and or/width of the implant 100, while in some embodiments, the thickness dimension can vary along the length and/or width of the implant 100. For example, some portions of the implant 100 can be thicker than other portions. In certain cases, the thicker portions may be positioned to correspond with regions of greater fat pad atrophy. In some embodiments, the thickness of the implant 100 can be adjusted, for example, by varying the amount of filler (discussed below) used therein.

As illustrated in FIGS. 1A, 1B, and 2, in some embodiments, the implant pad of the implant 100 can comprise a substantially circular or oval shape. As described below, other shapes can be used. The implant pad of the implant 100 can be configured to cover a single or multiple metatarsals or regions of fat pad atrophy. The implant pad of the implant 100 can be configured to extend substantially across the width of the foot 10 (as shown in FIG. 1A) below the first through fifth metatarsals 20a-20b. In some embodiments, the implant 100 can be configured such that the major axis of the implant pad is substantially aligned across the width of the foot 10 (for example, as shown in FIG. 1A). In some embodiments, the implant 100 can be configured such that the major axis of the implant pad is substantially aligned along the length of the foot 10 (for example, as shown in FIG. 2). However, other alignments for the implant pads of the implant 100 can be used. For example, the implant 100 of FIG. 2 can be aligned such that the major axis of the implant pad extends across the width of the foot 10. As noted previously, the oval shape of the implant pad of the implant 100 illustrated in FIGS. 1A, 1B, and 2 is provided by way of example only. Other shapes for the implant pad of the implant 100 can be used.

In some embodiments, the implant 100 is installed at the ball of the foot. For example, the implant 100 can be installed below the phalanges and/or metatarsals of the foot, below and/or behind the heads of the metatarsals, below and/or behind the metatarsophalangeal joint and/or can overlap with the phalanges and/or metatarsals.

In some cases, the implant 100 can be installed at or below the heel of the foot, such as below the calcaneus of the foot. In some embodiments, the implant 100 is implanted close to the floor of the foot. For example, the implant 100 can be positioned approximately 2 mm, 4 mm, 6 mm, 8 mm, 10 mm, or more above the bottom surface of the foot. In some embodiments, the implant 100 can be contoured for use in the heel of the foot. For example, the implant 100 may comprise a wedge shape or depression that complements the shape of the calcaneus such that the calcaneus can rest within the wedge or depression. As noted previously, the implant 100 can be used in other locations as well, such as the arch of the foot, the hands, or other locations of the body.

The implant 100 can be anchored, using sutures, mechanical fasteners (such as bone screws), and/or surgical adhesives to the bones (for example, the metatarsals or calcaneus) and/or soft tissues (for example, the plantar fascia) of the foot. In some embodiments, the implant 100 is anchored in place with bone screws attached to bone (for example, the metatarsals or calcaneus) and surgical adhesive attached to the plantar fascia. Other methods for anchoring the implant 100 are described throughout the application.

Figure 3A:
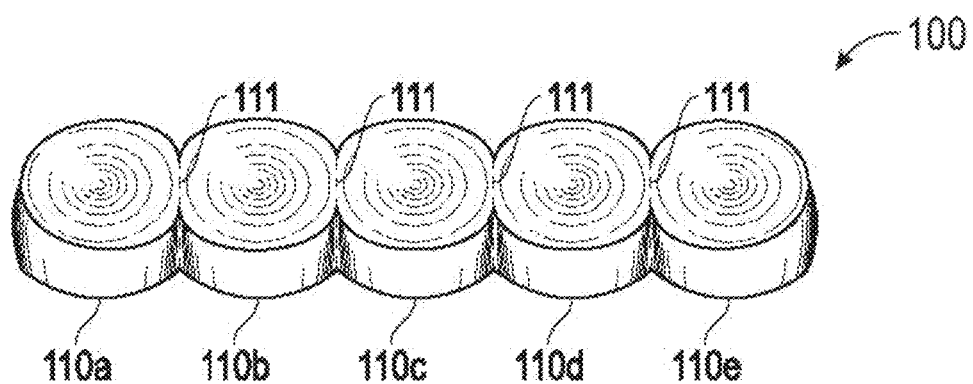
FIG. 3A is a diagram illustrative of an embodiment of an implant that includes five conjoined implant pads.

FIG. 3A is a diagram illustrative of an embodiment of the implant 100 that includes five implant pads 110a-110e (generically referred to as implant pad 110) conjoined together. In some embodiments, each of the implant pads 110a-110e can be configured in size and shape to correspond to the metatarsals 20a-20e (see FIG. 1A) or fat pad that an implant pad 110 is to replace, such that, for example, the implant pad 110a can be positioned below the first metatarsal 20a, the implant pad 110b can be positioned below the second metatarsal 20b, the implant pad 110c can be positioned below the third metatarsal 20c, the implant pad 110d can be positioned below the fourth metatarsal 20d, and the implant pad 110e can be positioned below the first metatarsal 20e. However, it will be understood that a variety of shapes and sizes can be used for the implant pads 110a-110e.

Although FIG. 3A illustrates five conjoined implant pads 110a-110e, any number of implant pads 110 can be used. In some embodiments, the implant 100 can include between two and ten implant pads 110. In some embodiments, the number of implant pads 110 is configured to correspond to the number of metatarsals below which the implant 100 will be positioned. For example, if the region to be treated is below the first, second, and third metatarsals 20a-20c, the implant 100 can include three implant pads 110a-110c.

In some embodiments, the implant pads 110a-110e are conjoined along a straight line (for example, as shown in FIG. 3A). In some embodiments, the implant pads 110a-110 are conjoined along a curved line. The curved line can be configured to follow the contour of the foot. For example, in many cases the first metatarsophalangeal joint is positioned more towards the front of the foot than the fifth metatarsophalangeal joint. The curved line can be configured to pass over each of the first through fifth metatarsophalangeal joints (or a portion thereof, such as the first through third, or second through fifth, etc.). Furthermore, in some cases, the implant pads 110a-110e can be conjoined at different locations to form a stepped line with different offsets between the different implant pads 110a-110e.

In some embodiments, each of the implant pads 110a-110e is conjoined to an adjacent implant pad 110a-110e at an interface 111. In some embodiments, the interface 111 is permeable, such that a filler within the implant 100 (discussed below) can flow between adjacent implant pads 110. In some embodiments, the interface 111 is semi-permeable, such that the flow of a filler within the implant 100 is restricted. In some embodiments, the interface 111 comprises an impermeable barrier. In some embodiments, the interface 111 can be completely open. For example, in some embodiments, the interface 111 can comprise an opening between each adjacent implant pads. In some embodiments, the interface 111 comprises a perforation (or other structure) which allows adjacent implant pads to be severed from each other. This can allow a doctor to adjust the length and number of implant pads to suit a particular treatment.

Although the implant pads 110a-110e are illustrated in FIG. 3A as being approximately the same size, it will be understood that the relative sizes of the implant pads 110a-110e can vary. For example, the first implant pad 110a can be larger than the second implant pad 110b (or vice versa), and so on. In some embodiments, the size and shape of each implant pad 110a-110e can correspond to the size and shape of the fat pad that the implant pad is replacing or supplementing. In some embodiments, the size and shape of each implant pad 110a-110e can correspond to the amount of deterioration or atrophy of the fat pad that the implant pad 110a-110e is replacing or supplementing.

Figure 3B:
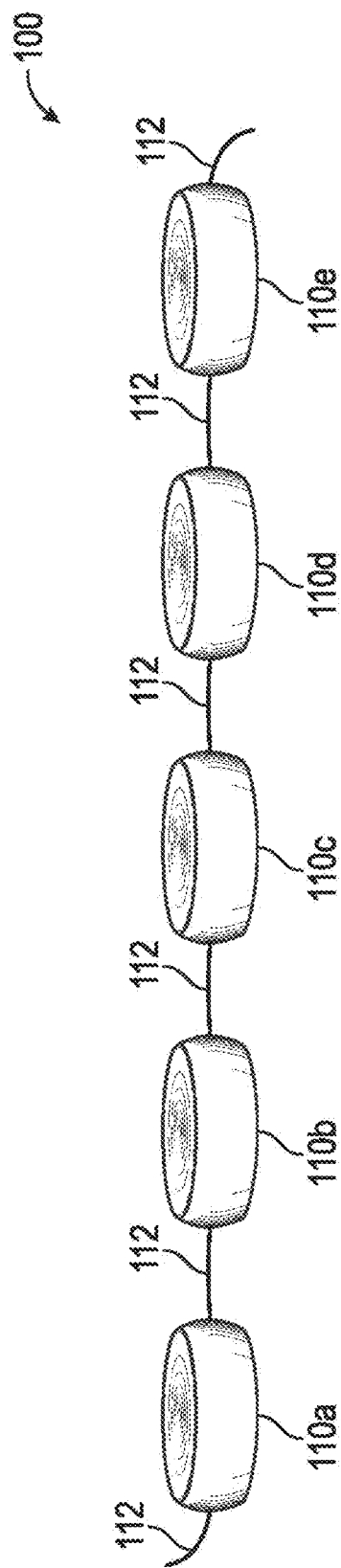
FIG. 3B is a diagram illustrative of an embodiment of an implant that includes five implant pads spaced along a connecting member.

FIG. 3B is a diagram illustrative of an embodiment of an implant 100 that includes five implant pads 110a-110e spaced along a connecting member 112. In some embodiments, the connecting member 112 can comprise a string, thread, wire, band, ribbon, etc., or other similar structure. In certain embodiments, the connecting member 112 can comprise the same material as the exterior lining (discussed below) of the implant 100. In some embodiments, the connecting member 112 comprises a flexible or a rigid material. In some embodiments, the connecting member 112 comprises a pliable material that maintains its shape once deformed. For example, a doctor can shape the implant 100 by deforming the pliable material of the connecting member into a desired shape, and, once installed, the connecting member 112 may substantially retain that shape. In some embodiments, the connecting member 112 can comprise a tube such that filler can flow between adjacent implant pads. In some embodiments, the tube can include a semi-permeable membrane that restricts flow between the implant pads.

As described in greater detail above, in some embodiments, each of the implant pads 110a-110e can be configured in size and shape and spaced along the connecting member 112 to correspond to the position of the metatarsals 20a-20e (see FIG. 1A), such that, an implant pad 110 can be positioned below each metatarsal 20 that is to be treated. In some embodiments, the spacing between implant pads is uniform. In certain embodiments, the spacing between implant pads is not uniform. For example, the spacing can be configured to correspond to the distance between adjacent metatarsophalangeal joints. In some embodiments, the spacing may be configured such that one or more implant pads may be positioned in the ball of the foot and be connected, via connecting member 112, to one or more additional implant pads in the heel of the foot.

Although FIG. 3B illustrates five implant pads 110a-110e spaced along the connecting member 112, other numbers of implant pads 110 can be used. In some embodiments, the implant 100 can include between two and ten (or some other quantity) implant pads 110. In some embodiments, the number of implant pads 110 is configured to correspond to the number of metatarsals below which the implant 100 will be positioned. For example, if the region to be treated is below the first, second, and fourth metatarsals 20a, 20b, 20d, the implant 100 can include three implant pads 110a, 110b, 110d spaced along the connecting member 112. In the illustrated embodiment, the connecting member 112 extends beyond the first and fifth implant pads 110a, 110e. In some embodiments, the additional length of the connecting member 112 can be used to mount the implant 100 to the foot. For example, the additional length of the connecting member can be mounted to the side of the first and fifth metatarsal or other location as desired. In addition, it will be understood that in certain embodiments, the connecting member 112 can terminate at the last implant pad on either side of the implant 100.

In some embodiments, the connecting member 112 is configured to be severable, such that the length of the implant 100 and/or the number of implant pads can be adjusted. This can allow a doctor to adjust the length of the implant 100 and/or number of implant pads to suit a particular treatment. As mentioned above, although illustrated in FIG. 3B as being the same size, it will be understood that the relative sizes of the implant pads 110a-110e can vary as desired.

Figure 3C:
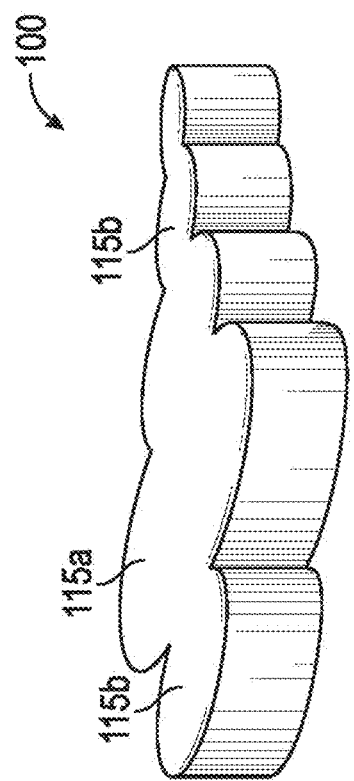
FIG. 3C is a diagram illustrative of an embodiment of an implant that comprises a non-geometric shape.

FIG. 3C is a diagram illustrative of an embodiment of an implant 100 that comprises a non-geometric shape. As used herein, the term "non-geometric shape" is intended to signify any non-standard or irregular shape. For example, as illustrated in FIG. 3C, the implant 100 comprises a shape with a larger portion 115a and smaller portions 115b. In some embodiments, the configuration of the larger portion 115a and smaller portions 115b can correspond to the shape of the fat pad. In some embodiments, the configuration of the larger portion 115a and smaller portions 115b can correspond to levels of atrophy within a fat pad or desired size of the implant pad 110 for a particular region. For example, larger portion 115a can be configured for placement in a region of greater fat pad atrophy (or greater desired size) and smaller portions 115b can be configured for placement in regions of lesser fat pad atrophy (or lesser desired size). In the illustrated embodiment of FIG. 3C, the implant 100 is configured for treatment of advanced fat pad atrophy of the second metatarsal 20b. Thus, the larger portion 115a is configured for positioning proximate to the second metatarsal 20b. Other non-geometric shapes can be used. For example, the larger portion 115a can be configured for placement below the first metatarsal 20a. The non-geometric shapes can be configured to form a single continuous implant of non-standard shape that can cover a single or multiple metatarsals.

In some embodiments, the implant 100 can comprise a customizable shape. For example, in some embodiments, the implant 100 can be made of a malleable material. A doctor may form the implant into a desired shape configured for a particular treatment. In some embodiments, the implant 100 may be configured to maintain a particular custom shape once formed. For example, the material can be cured such that it substantially retains the molded shape. In some embodiments, the implant 100 may be configured such that a doctor can cut, trim, or sculpt the shape of the implant. For example, a doctor may cut the implant 100 to a desired shape suitable for a particular treatment. In some embodiments, the shape of the implant 100 can be customized by varying the amount of filler in the implant.

Returning to FIG. 1A, the implant 100 can comprise an exterior lining 105 (or shell) surrounding a cavity 107. The lining 105 can be pliable and can be made from elastomer silicone, plastic, rubber, or other suitable material, such as, but not limited to graphene, ultra-high molecular weight polyethylene, Kevlar, Technora, Nomex, a non-Newtonian material, a material that becomes more rigid under stress or force, or any combination thereof, etc. In some embodiments, suitable materials can include those that are biocompatible with the human body and/or that can withstand the forces and pressures experienced by the foot. In some embodiments, suitable materials include materials with relatively high tensile strength. For example, in some embodiments, the lining 105 comprises a material with a tensile strength of at least approximately 2800 PSI, 2000 PSI, 1000 PSI, or 700 PSI. The lining 105 of implant 100 can be configured to substantially prevent, mitigate, or reduce the likelihood of rupture. As discussed below, the implant 100 can include additional features that strengthen the implant 100 against rupture. In some embodiments, the lining 105 is configured to dissipate force (for example, impact forces common in the foot).

In some embodiments, the lining 105 can comprise a plurality of layers. In some embodiments, each layer of the lining 105 comprises a different resonant frequency than the other layers. In some embodiments, the lining 105 comprises two, three, or more layers. In some embodiments, the layers of the lining 105 comprise fibers. In some embodiments, the fibers of each layer of the lining 105 are oriented in a different direction than the fibers of the remaining layers of the lining 105. In some embodiments, the lining 105 comprises a woven structure. The lining 105 can be configured to dissipate forces over a large area. In some embodiments, each layer of the lining 105 comprises a material with a resonant frequency different than that of the other layers. This can allow the implant 100 to absorb and depress force as it travels across or through the implant 100.

As illustrated in FIGS. 1A and 1B, in some embodiments, the implant 100 includes a lining 105 that defines a cavity 107. In some embodiments, the cavity 107 comprises a liquid or semi-liquid filler material, such as a saline solution, a silicone gel, or other suitable filler material, such as a liquid with a higher viscosity than water. Suitable filler materials can include liquids or semi-liquids that are biocompatible with the human body. In some embodiments, the filler for the cavity 107 need not be biocompatible.

In some embodiments, the implant filler can be a substance that, while liquid when injected, becomes solid or semi-solid within the implant, thereby decreasing the chance of leakage should the implant lining 105 be punctured or otherwise compromised. In certain embodiments, a non-Newtonian liquid may be used as the filler, allowing the material to be injected into the implant and modified through the implants ports and valves; however, under pressure, the implant material can behave as a solid and give support to the implant area. In certain cases, a shear-thickening/thinning gel, solid, or plastic, such as D30 or Deflexion can be used for the exterior lining 106, interior filler, and/or for the entire implant 100. These materials strengthen under pressure due to their polymer structure. In another embodiment, the implant filling may also be a material that is solid without pressure and liquefies under pressure.

In some embodiments, the implant 105 includes additional internal features (in other words, within the cavity 107 defined by the lining 105) that can strengthen the implant 100 against rupture. Several of these features that can be included in some embodiments of the implant 100 will now be described with reference to FIGS. 4A to 4G. Furthermore, it will be understood that any of the embodiments described herein with reference to the interior structure can be combined with the aforementioned embodiments of the implant 100. In addition, in certain embodiments, the embodiments described herein with reference to the interior structure can be used in combination. For example, the interior structure can include walls that traverse from one end of the lining to the other, walls that do not, concentric chambers, a matrix structure, netting, and/or semi-permeable walls, etc.

Figure 4A:
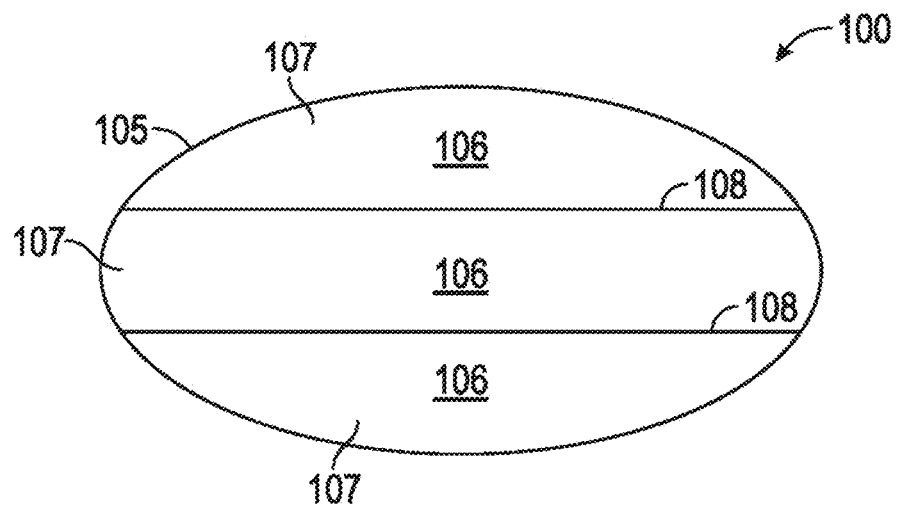
FIG. 4A is a diagram illustrative of an embodiment of an implant pad of an implant that includes three internal chambers.

FIG. 4A is a diagram illustrative of a cross-sectional view of an embodiment of an implant pad of the implant 100 that includes three internal chambers 106. The chambers 106 are separated by walls 108. Each chamber 106 of the cavity 107 can include the filler material. In some cases, different chambers 106 can include a different filler. For example, the outer chambers 106 can include a filler with a higher or lower viscosity than the filler in the center chamber 106. In certain cases, some chambers 106 can include a non-liquid polymer while other chambers 106 can include a liquid filler.

In some embodiments, the walls 108 comprise the same material as the lining 105. In certain embodiments, the walls 108 comprise a material different than that of the lining 105. In some embodiments, the walls 108 comprise a permeable material, such that the filler can flow between the chambers 106. In some cases, the walls 108 comprise a semi-permeable material, such that the flow rate of the filler through the walls 108 is restricted. In some embodiments, the walls 108 comprise an impermeable material, such that the filler is prevented from flowing between chambers 106.

Although three chambers 106 are illustrated in FIG. 4A, more or fewer chambers 106 can be used. For example, in some embodiments, the implant 100 can include between one and ten or more chambers 106. Further, the arrangement of the chambers 106 in FIG. 4A is merely provided by way of example and other arrangements can be used. For example, in some embodiments, the walls 108 defining the chambers 106 need not be parallel. Additionally, the chambers 106 can be configured to extend in any direction (for example, longitudinally, latitudinally, diagonally, etc.). The chambers 106 can extend partially across or entirely across the implant 100. In some embodiments, the size or volume of the chambers 106 are approximately equal. In some embodiments, the chambers 106 comprise different sizes or volumes. Further, the implant 100 can comprise any number or combination of different chambers 106. For example, the implant can comprise one or more longitudinally extending chambers 106 and one or more latitudinally extending chambers 106.

In some embodiments, the lining 105 and/or each of the walls 108 can comprise multiple materials, each having a different resonant frequency. In some cases, the resonant frequencies can be in tune with the expected force to be dissipated, which will allow the force to be dampened as it passes from one layer to another. This can allow the implant 100 to absorb and depress force as it travels across or through the implant 100. Non-limiting examples of materials that can be used for the walls 108 include, but are not limited to, graphene, Kevlar, Technora, and/or Nomex, any combination thereof, etc. In some embodiments, the walls 108 can comprise any of the materials discussed above in relation to the lining 105.

Figure 4B:
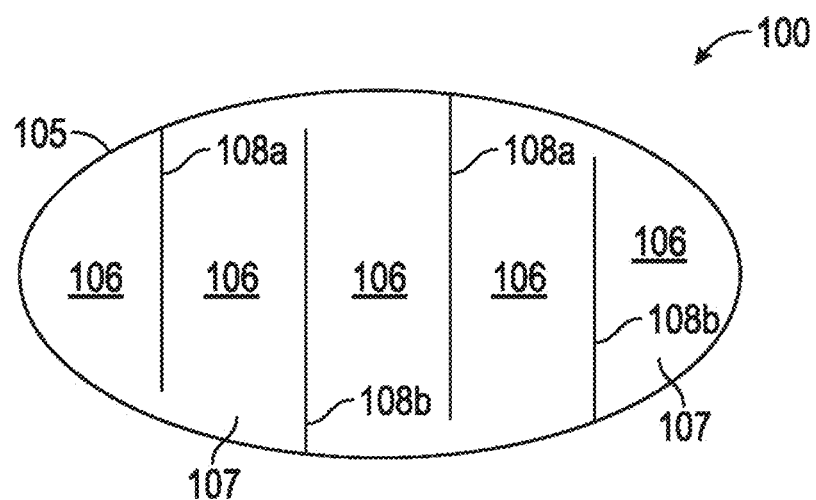
FIG. 4B is a diagram illustrative of an embodiment of an implant pad of an implant that includes alternatingly connected interior walls.

FIG. 4B is a diagram illustrative of a cross-sectional view of an embodiment of an implant 100 that includes alternatingly connected interior walls 108a, 108b. The walls 108a, 108b partially define chambers 106 within the cavity 107. In the illustrated embodiment, the implant includes five chambers 106, although other numbers can be used. The chambers 106 can be filled with the filler. As shown in FIG. 4B, the walls 108a are connected to a first side of the implant 100 and are not connected to a second side (opposite the first side) of the implant 100. The walls 108b are positioned between the walls 108a and are alternatingly connected to the implant 100. That is, the walls 108b are connected to the second side of the implant 100 and are not connected to the first side of the implant 100. Because each of the walls 108a, 108b includes an opening between adjacent chambers 106, the filler is able to flow between adjacent chambers 106. However, because the openings alternate between opposing sides of the implant 100, the flow of the filler material is somewhat restricted. Each of the walls 108a, 108b can comprise an impermeable, semi-permeable, or permeable material. The walls 108a, 108b can extend in any direction (for example, longitudinally, latitudinally, diagonally, etc.) or any combination thereof. In some embodiments, the lining 105 and/or each of the walls 108a, 108b can comprise multiple materials with different resonant frequencies. This can allow the implant 100 to absorb and depress force as it travels across or through the implant 100. In some embodiments, the implant 100 can comprise alternatingly connected interior walls 108a, 108b defining partially enclosed cavities 106 and fully connected interior walls 108 defining enclosed cavities 106.

Figure 4C:
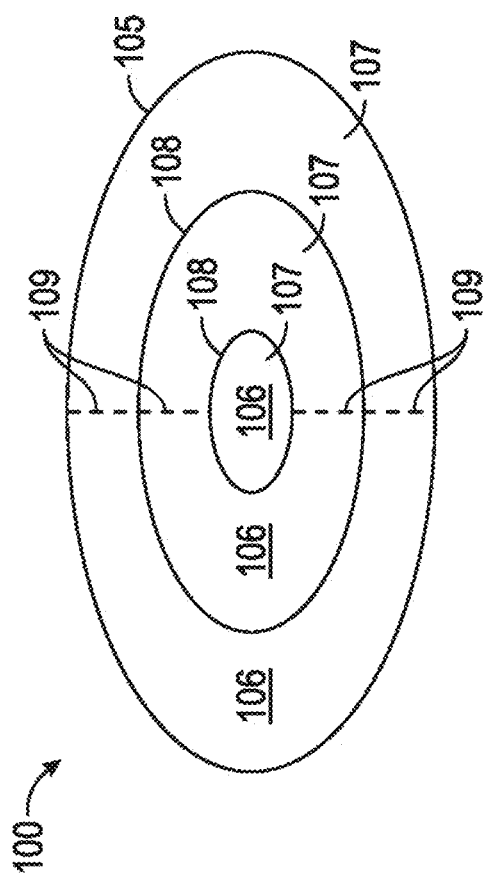
FIG. 4C is a diagram illustrative of an embodiment of an implant pad of an implant that includes concentrically arranged internal chambers.

FIG. 4C is a diagram illustrative of a cross-sectional view of an embodiment of an implant 100 that includes substantially concentrically arranged internal chambers 106. The chambers 106 are separated by walls 108. The chambers 106 can include the filler. In some cases, different chambers 106 can include a different filler. For example, the outer chambers 106 can include a filler with a higher or lower viscosity than the filler in the center chamber 106. In certain cases, some chambers 106 can include a non-liquid polymer while other chambers 106 can include a liquid filler.

Although three chambers 106 separated by two walls 108 are illustrated in FIG. 4C, other numbers of chambers 106 and walls 108 can be used. For example, in some embodiments, multiple smaller chambers can be located together in a larger chamber. Further, in some embodiments, the size of the chambers 106 and the spacing between walls 108 is not uniform. Each of the walls 108 can comprise an impermeable, semi-permeable, or permeable material. In some embodiments, the lining 105 and/or each of the walls 108 can comprise a material with a different resonant frequency. This can allow the implant 100 to absorb and depress force as it travels across or through the implant 100. In some embodiments, the walls 108 can be connected to each other and/or the lining 105 by connectors 109. The connectors 109 can be configured to maintain the relative positioning of the various chambers 106. The connectors 109 comprise walls, strings, wires, strands, or other suitable structures. In some embodiments, the connectors 109 comprise the matrix structure 200 or netting 300 described below with reference to FIGS. 4E and 4G.

Figure 4D:
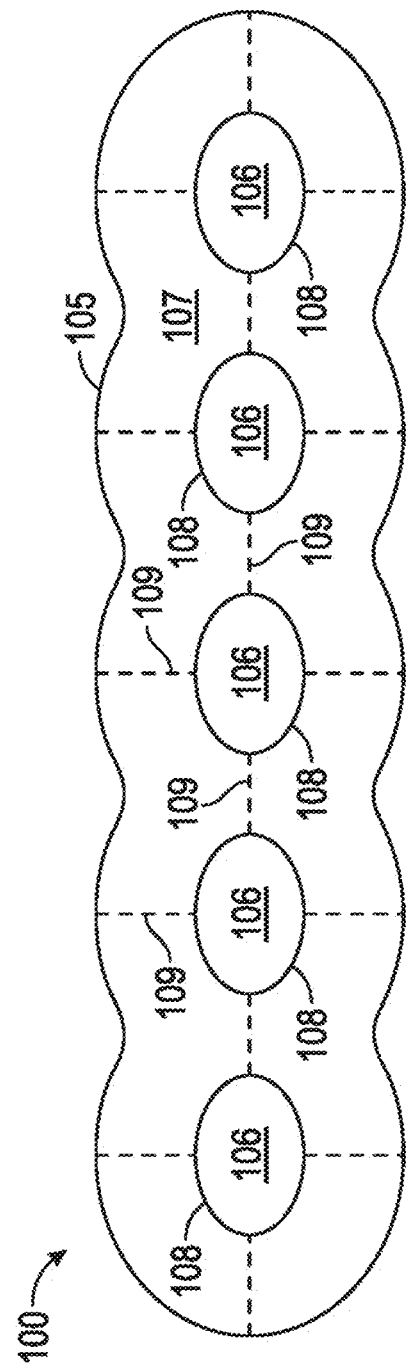
FIG. 4D is a diagram illustrative of an embodiment of an implant pad of an implant that includes five internal chambers.

FIG. 4D is a diagram illustrative of a cross-sectional view of an embodiment of an implant 100 that includes five internal chambers 106 disposed within the cavity 107. The chambers 106 are defined by walls 108. In some cases, different chambers 106 can include a different filler and/or the chambers 106 can include a different filler than the cavity 107. For example, the chambers 106 can include a filler with a higher or lower viscosity than the filler in the center cavity 107. In certain cases, the chambers 106 can include a non-liquid polymer while the cavity 107 can include a liquid filler, or vice versa.

The five internal chambers 106 can be configured in size and shape to correspond to the size and/or positioning of the fat pads of the first through fifth metatarsals 20a-20d. In some embodiments, other numbers of internal chambers 106 (for example, two, three, four, six, seven, etc.) can be used. Each of the walls 108 can comprise an impermeable, semi-permeable, or permeable material. In some embodiments, the lining 105 and/or each of the walls 108 can comprise a material with a different resonant frequency. This can allow the implant 100 to absorb and depress force as it travels across or through the implant 100. In some embodiments, the walls 108 can be connected to each other and/or the lining 105 by connectors 109. The connectors 109 can be configured to maintain the relative positioning of the various chambers 106. The connectors 109 comprise walls, strings, wires, strands, or other suitable structures. In some embodiments, the connectors 109 comprise the matrix structure 200 or netting 300 described below with reference to FIGS. 4E and 4G. It will be understood that any combination of the aforementioned embodiments can be used together. For example, multiple chambers 106 can be created using longitudinal/latitudinal walls and/or concentric walls, as discussed above.

Figure 4E:
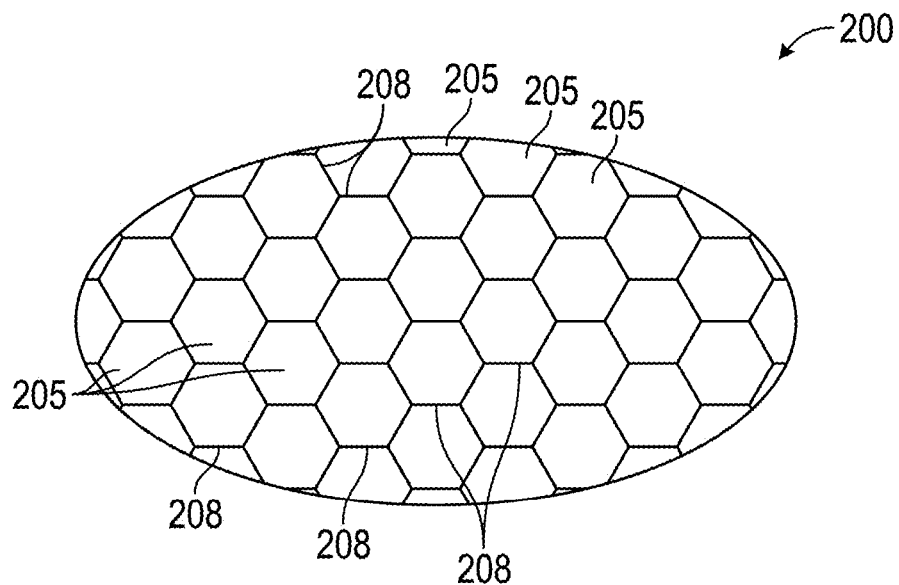
FIG. 4E is a diagram illustrative of an embodiment of a matrix structure included in some embodiments of an implant pad of an implant.

FIG. 4E is a diagram illustrative of an embodiment of a matrix structure 200 that can be included in the implant 100. The matrix structure 200 can be included, for example, in the interior cavity 107 and/or chambers 106 of any of the embodiments discussed above. In some embodiments, the matrix structure 200 can be included in some of the chambers 106, but not others. For example, an outer chamber 106 can include the matrix structure 200 and the inner chamber can omit it, or vice versa. Similarly, in certain cases, the matrix structure 200 can be used in conjunction with an implant filler or can be used without an implant filler.

The matrix structure 200 comprises a matrix of cells 205 separated by walls 208. In the illustrated embodiment, the cells 205 of the matrix structure 200 comprise a hexagonal cross-sectional shape. However, it will be understood that a variety of shapes can be used as desired, such as spherical, trapezoidal, square, or rectangular, etc. In some embodiments, the size and shape of the cells 205 can be uniform. In some embodiments, the size and shape of the cells 205 is not uniform. In some embodiments, the cells 205 have a volume of less than approximately 1, 0.5, 0.25, 0.1, or 0.05 cubic centimeters. The matrix structure 200 can be used as the connectors 109 discussed above.

In some embodiments, the matrix structure 200 strengthens the implant 100 against rupture and/or assists in the dissipation of forces experienced by the implant 100. For example, the matrix structure can be configured to radiate and dissipate forces. The number and/or size of the cells can be related to the ability of the matrix structure 200 to dissipate force. For example, in some embodiments, when the matrix structure comprises greater numbers of smaller cells per unit of volume, the matrix structure may dissipate more force through the walls of the cells. In some embodiments, when the matrix structure comprises fewer numbers of larger cells per unit volume, the matrix structure may dissipate more force through the filler of the cells. Thus, the force dissipation characteristics of the matrix structure 200 can be adjusted by varying the size and number of the cells, as well as the material of the cell walls and the filler.

In some cases, the matrix walls 208 can also be made of one or more layers of material (homogenous or heterogeneous). The layers of material can have different resonant frequencies in tune to the expected force that is to be dissipated, which will allow the force to be dampened as it passes from one layer to another and from one wall 208 to another wall 208. In some embodiments, the walls 208 between the cells 205 can comprise an impermeable, semipermeable, or permeable material. In some embodiments, the walls 208 comprise a porous material. Non-limiting examples of materials that can be used for the walls 108 include, but are not limited to, graphene, Kevlar, Technora, and/or Nomex, any combination thereof, etc. In some embodiments, the walls 208 can comprise the same material (or any of the same materials) as the lining 105 described above.

Figure 4F:
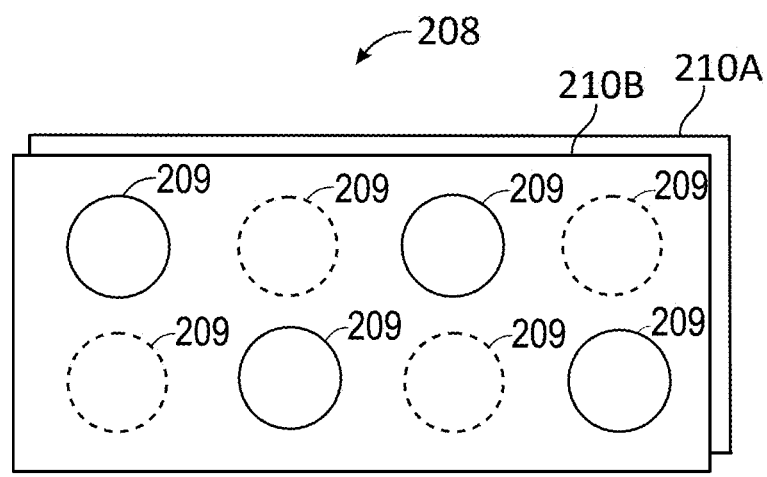
FIG. 4F is a diagram illustrative of an embodiment of a porous wall for use within an implant pad.

In the illustrated embodiment of FIG. 4F, the wall 208 can include one or more openings 209 disposed therein. The openings 209 can allow the filler material to flow between the cells of the matrix structure 200. The porosity of the wall 208 can be varied according to the number and/or size of the openings 209. In some embodiments, the wall 208 can comprise a plurality of layers, with each layer including openings 209. The porosity of the wall 208 can further be varied by offsetting the openings 209 of adjacent layers (e.g., layers 210A, 210B) such that flow through the openings 209 is restricted as the filler changes direction as it crosses the different layers. The openings 209 and/or the offset between the openings 209 in adjacent layers (e.g., layers 210A, 210B) of the wall 208 can create turbulence and vortex that makes it difficult for the filler to move through the cells of the matrix. Similar openings or layers of walls comprising offset openings can be used with the walls 108 of the different chambers.

Figure 4G:
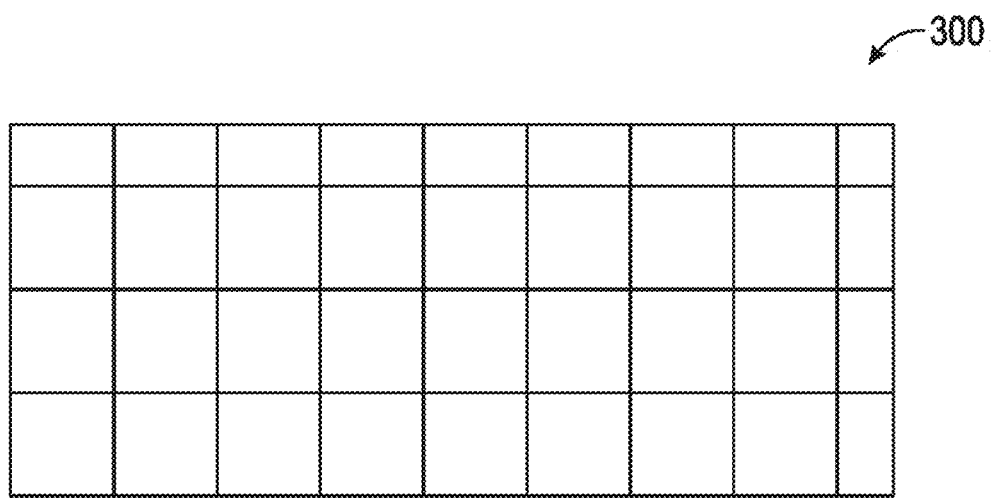
FIG. 4G is a diagram illustrative of an embodiment of a netting included in some embodiments of an implant pad.

FIG. 4G is a diagram illustrative of an embodiment of a netting 300 included in some embodiments of the implant 100. The netting 300 can be included, for example, in the interior cavity and/or chambers 106 of any of the embodiments of the implant 100 discussed above. The netting 300 can include multiple walls and/or lines of materials of inside the implant 100. In some embodiments, the netting 300 can be substantially porous, allowing the filler to move between chambers 106 or cells. In some embodiments, the netting 300 can serve as the connectors 109 discussed above.

In some embodiments, the chambers 106 and/or cells of the implant 100 can be filled with the filler during manufacture of the implant 100. In some embodiments, the chambers 106 and/or cells of the implant 100 can be filled with the filling during installation, for example, as part of the installation surgery. In some embodiments, the implant 100 is surgically inserted in the foot 10 in an unfilled state and filled with the filler during the surgery.

In some embodiments, the implant 100 comprises a solid material, rather than a liquid filler. The solid material can be rigid, pliable, and/or flexible. In certain embodiments, a non-Newtonian material can be used. In some embodiments, the implant 100 comprises one or more solid materials. For example, the implant 100 can comprise a plurality of layers of solid material, such as a multiple stratified layers of the material described above for the external lining 105. In some embodiments, such as when each lining uses multiple layers of different materials, at least two of the materials used in the lining can have a different resonant frequency. In some cases, each material used in a lining can have a different resonant frequency. The resonant frequency of a particular material can be tuned to the expected force that the material is expected to dissipate.

In some embodiments, the layers can comprise fibers. In some embodiments, the fibers of each layer are oriented in a different direction than the fibers of an adjacent layer and/or of the remaining layers. In some embodiments, one or more of the solid materials comprises a woven structure.

In some embodiments, the implant 100 can comprise one or more layers of graphene, Kevlar, Technora, and/or Nomex, or any combination thereof without any filler material. In some embodiments, an ultra-high molecular weight polyethylene can be woven into the fabric. In some embodiments, the implant 100 can be configured to radiate and spread pressure from one location to another. For example, if the region of greatest atrophy is located below the second metatarsal head, the implant 100 can be configured to dissipate forces acting on the second metatarsal head to other metatarsals or other locations of the foot. In some embodiments, the solid implant 100 can be substantially firm. In some embodiments, the solid implant can be thin, for example, less than approximately 5 mm, 2.5 mm, 1 mm, or 0.5 mm.

In some embodiments, the exterior of the implant 100 can comprise an impermeable material. In certain embodiments, the exterior of the implant 100 can comprise a permeable or a porous material.

The exterior surface of the implant 100 can include features configured to prevent migration of the implant 100 after surgical installation. Because the foot 10 (or other locations where the implant 100 can be surgically installed) undergoes a wide range of movements and motions and is subjected to high and highly variable forces, the implants or injected material in the foot can be susceptible to migration. For example, one problem that can arise with when injecting a material, like silicone, into the foot is that over time the silicone can dissipate and/or migrate away from the location where it was originally injected. Conversely, the implant 100 can be configured to substantially prevent, reduce, or mitigate migration of the implant 100.

For example, in some embodiments, the exterior surface of the implant 100 includes one or more textures configured to prevent, reduce, or mitigate migration. For example, the exterior surface of the implant 100 can have a high friction, rough, or patterned texture that resists migration of the implant 100 after installation. In some embodiments, the exterior surface of the implant 100 includes an abrasive surface. The abrasive surface can be configured to generate friction to resist migration of the implant 100. Several embodiments of example surface textures for the implant 100 will now be described. Furthermore, it will be understood that any of the embodiments described herein with reference to the exterior texture can be combined with the aforementioned embodiments of the implant 100. In addition, in certain embodiments, the embodiments described herein with reference to the exterior textures can be used in combination. For example, the exterior structure can include depressions, protrusions, cross-hatch texture, and/or multi-directional patterns, etc.

In some embodiments, the exterior surface of the implant 100 is configured with a plurality of hooks and/or loops extending therefrom. The hooks and/or loops can be rigid or flexible. The hooks and/or loops can be configured to grip or affix to the tissues, bones, ligaments, tendons, etc., surrounding the implant 100 to resist migration of the implant 100. In some embodiments, the hooks and/or loops can approximate the texture and function of a hook and loop fastener. In some embodiments, the exterior surface of the implant 100 is configured with a netting or net-like structure. The netting or net-like structure can be configured to provide friction and grab in order to resist migration of the implant 100.

In some embodiments, the exterior surface of the implant 100 can be configured with a shape or texture to engage with the structure of the plantar fat pad. For example, in some embodiments, the exterior surface can include depressions, or pores, to facilitate cellular growth and tissue connectivity. In some embodiments, the cellular growth can include collagen growth.

Figure 5A:
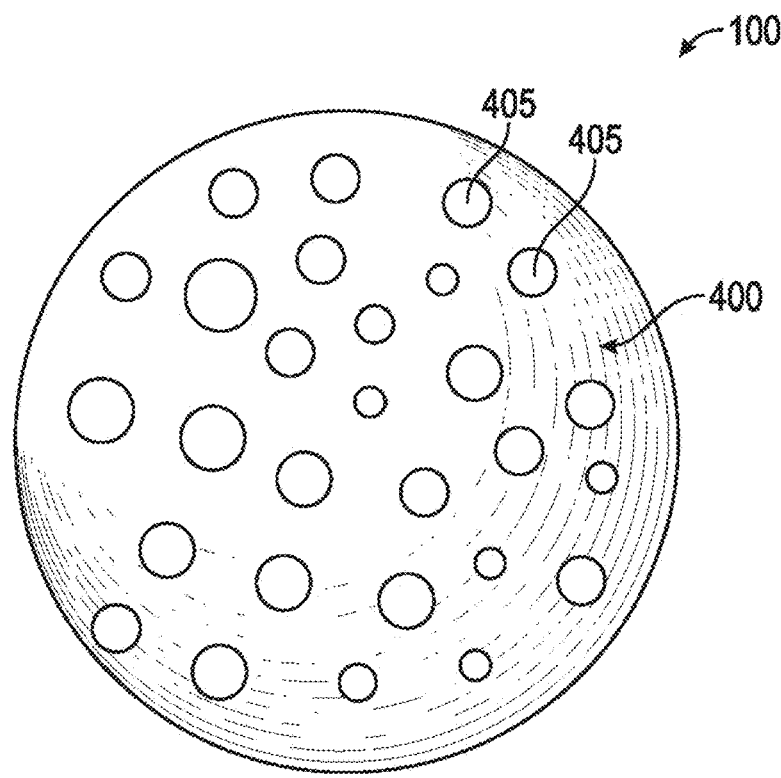
FIG. 5A is a diagram illustrative of an embodiment of an implant that includes an exterior texture with depressions.

FIG. 5A is a diagram illustrative of an embodiment of the implant 100 that includes an exterior texture 400 with multiple depressions 405 The depressions 405 can be uniformly sized and spaced or non-uniformly sized and spaced. In some embodiments, the exterior texture 400 is configured to facilitate cellular growth and tissue connectivity. For example, cells and/or tissue from body structures surrounding the installed implant 100 can grow into the depressions 405, thus stabilizing the implant 100 and preventing or reducing migration. In some embodiments, the exterior texture 400 is permeable or semi-permeable, allowing cells or tissue to grow into the interior of the implant. In some embodiments, the exterior texture 400 is not permeable and cellular or tissue growth is limited to interaction with the surface of the implant 100.

Figure 5B:
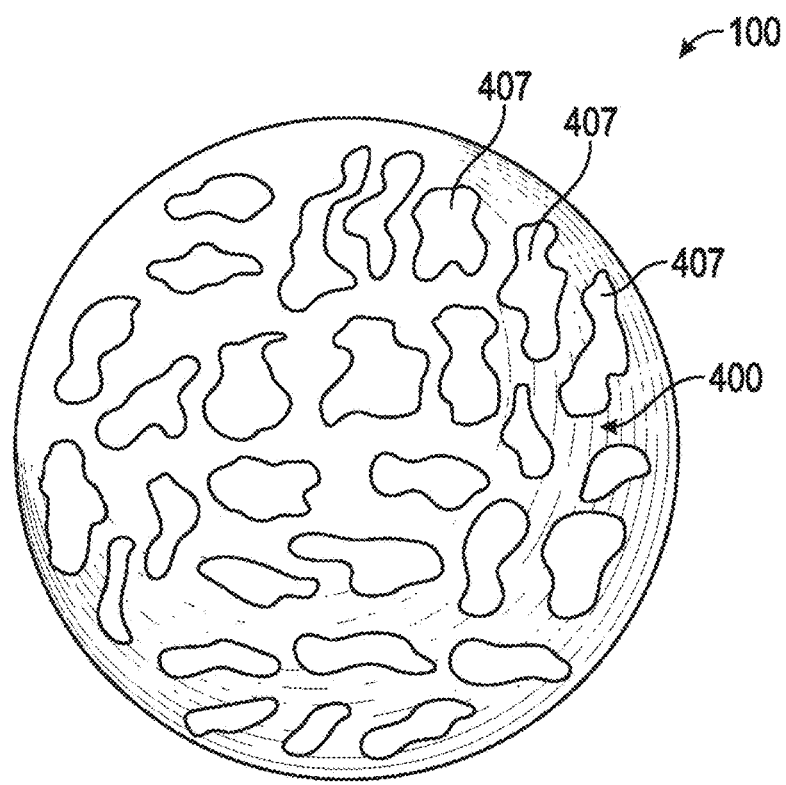
FIG. 5B is a diagram of an embodiment of an implant that includes an exterior surface with a texture that approximates the shape of fat globules.

FIG. 5B is a diagram of an embodiment of the implant 100 that includes an exterior surface with a texture 400 that include protrusions that approximate the shape of fat globules 407. In some embodiments, the exterior surface 400 can include a protrusions of non-geometric structures, providing friction and grab in order to resist migration of the implant 100. In some embodiments, the shape of the fat globules 407 or non-geometric structures can approximate the size and shape of the fat globules occurring in fat pads in the body. In this way, the exterior surface of the implant 100 can mesh or otherwise engage with the existing or remaining fat pads in the body when installed.

Figure 5C:
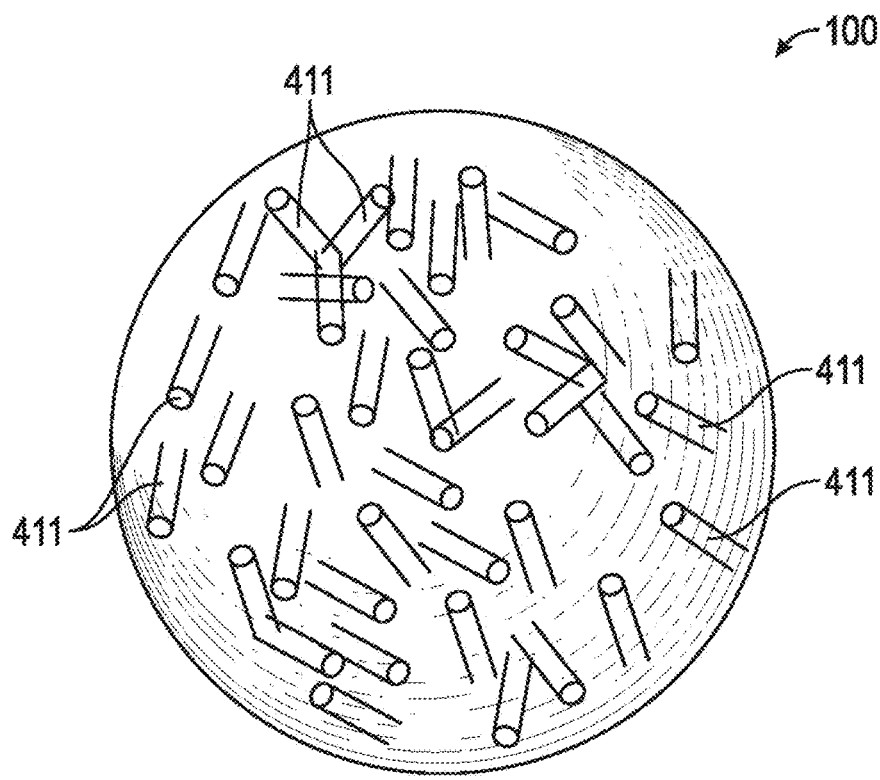
FIG. 5C is a diagram illustrative of an embodiment of an implant that includes protrusions extending from the exterior surface thereof.

FIG. 5C is a diagram of an embodiment of the implant 100 that includes protrusions 411 extending from the exterior surface thereof. In some embodiments, the exterior surface of the implant 100 can include finger-like protrusions extending therefrom. In some embodiments, the protrusions can extend in a variety of directions. The protrusions can comprise multi-directional fingers. The protrusions can be rigid or flexible. The protrusions can be configured to provide friction and grab to resist migration of the implant 100. The protrusions can be about 0.5 mm, 1 mm, 2 mm, 3 mm, 4 mm, 5 mm, or longer. The protrusions can extend in varying angles from the surface of the implant. In some embodiments, the protrusions cover substantially the entire exterior surface of the implant. The protrusions can provide additional friction and anchor points for securing the implant.

In some embodiments, the exterior surface of the implant 100 can be configured with a rough cross-hatch texture. The rough cross-hatch texture can be configured to provide friction and grab to resist migration of the implant 100. In some embodiments, the exterior surface 100 of the implant 100 can be configured with a chevron pattern. The chevron pattern can comprise a pattern of alternating ridges and valleys. The chevron pattern can be configured to provide friction and grab to resist migration of the implant 100.

Figure 5D:
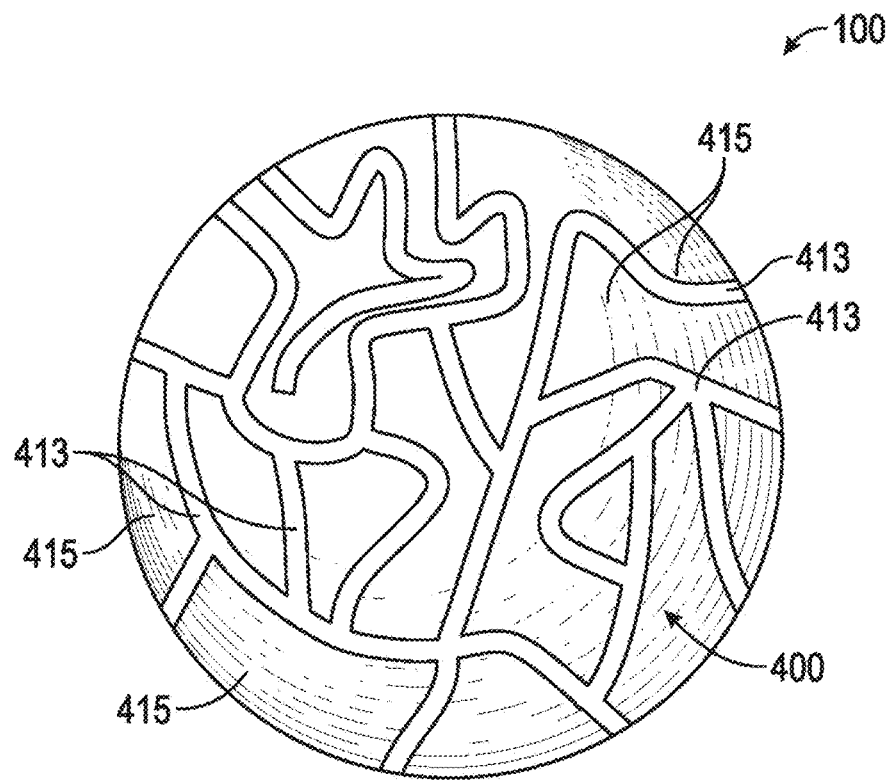
FIG. 5D is a diagram illustrative of an embodiment of an implant that includes an exterior surface with a multi-directional pattern.

FIG. 5D is a diagram illustrative of an embodiment of an implant 100 that includes an exterior surface with a multi-directional pattern 400, and in some cases a 360-degree pattern. The multi-directional pattern 400 can comprise multiple interconnected ridges 413 in different directions that are separated by valleys 415. In some cases, the ridges 413 and valleys 415 can give the appearance of a random pattern. The multi-directional pattern 400 can be configured to provide friction and grab along a plurality of different directions, and can resist migration of the implant 100.

In some embodiments, the exterior of the implant 100 can comprise a combination of the one or more of the textures described above. In some embodiments, one or more textures can be applied in an overlapping manner. For example, the exterior surface of the implant 100 can comprise a multi-directional pattern texture that includes a plurality of hooks and/or loops extending therefrom. In some embodiments, a plurality of textures can be implied on different portions of the exterior of the implant 100. For example, the portion of the exterior surface of the implant 100 that interfaces with hard tissue (non-limiting example: bone) can comprise a chevron texture and the portion of the exterior surface that interfaces with soft tissue (non-limiting example: fat, cartilage, tendons, ligaments, etc.) can comprise a texture of non-geometric structures, or vice versa. A wide variety of combinations of textures can be used. In some embodiments, the exterior of the implant 100 is configured with a smooth surface. The smooth surface can minimize friction.

Additionally or alternatively to the textured exterior surface described above, the implant 100 can include one or more features for anchoring the implant 100 in place. The implant 100 can be anchored to the soft tissue, bone, tendons, ligaments, etc., surrounding the implant 100 to prevent migration of the implant 100. The implant 100 can be secured in place using sutures, anchors (such as screws or other mechanical fasteners), surgical adhesives, or other suitable mechanisms. Furthermore, it will be understood that any of the embodiments described herein with reference to the exterior shape and anchoring portions can be combined with the aforementioned embodiments of the implant 100. In addition, in certain embodiments, the embodiments described herein with reference to the exterior shape and anchoring portions can be used in combination. For example, the implant 100 can include screw holes, a flap, one or more bands, one or more appendages, and/or one or more mounting plates.

Figure 6A:
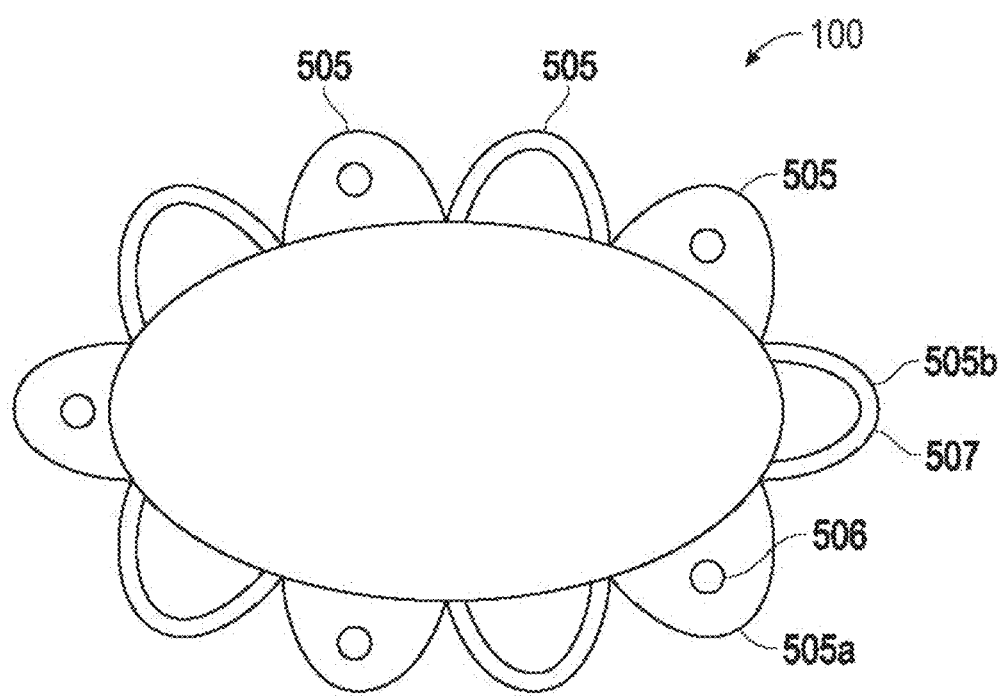
FIG. 6A is a diagram illustrative of an embodiment of an implant that includes attachment loops that can be used to secure the implant.

FIG. 6A is a diagram illustrative of an embodiment of the implant 100 that includes loops 505 that can be used to secure the implant. In some embodiments, the implant 100 includes one or more loops 505 extending therefrom. Various types of loops can be used. For example, in the illustrated embodiment of FIG. 6A, the loop 505a comprises a flap including a hole 506 extending therethrough. In some embodiments, the hole 506 can be reinforced with a grommet or washer. In some embodiments, the hole 506 can be omitted. Further, in the illustrated embodiment of FIG. 6A, the loop 505b comprises a band, string, wire, strand, or other similar structure 507 attached to the implant 100 at two separated locations so as to form the loop. The loops 505 can allow the implant 100 to be affixed via sutures, anchors (such as screws or other mechanical fasteners), adhesives, or other materials to bone, ligaments, the plantar fascia, tissue, or other foot structures surrounding the implant.

In some embodiments, the loops 505 can extend from the surface of the implant 100 around the periphery of the implant 100 (as shown in FIG. 6A). In some embodiments, the loops 505 can extend from other locations on the implant 100. The number, type, and position of the loops 505 can be varied without limitation. In some embodiments, one or more loops extend from each side of the implant 100 such that the implant 100 can be anchored in place from any side.

Figure 6B:
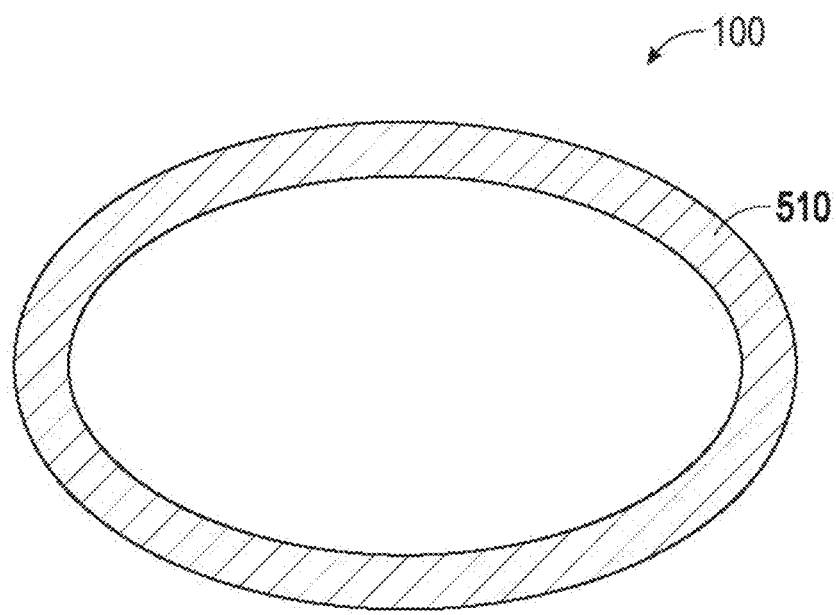
FIG. 6B is a diagram illustrative of an embodiment of an implant that includes a pierceable flap that can be used to secure the implant.

FIG. 6B is a diagram illustrative of an embodiment of the implant 100 that includes a flap 510 that can be used to secure the implant. The flap 510 can extend from the exterior of the implant 100 and allows the implant 100 to either be affixed via sutures, anchors (such as screws), adhesives, or other materials to bone, ligaments, the plantar fascia, tissue, or other foot structures surrounding the implant. In some embodiments, the flap 510 comprises a pierceable yet durable material. In some embodiments, the flap 510 comprises the one or more or a combination of the materials described above for the lining 105. In some embodiments, the flap 510 comprises the same material as the lining 105. In some embodiments, the implant 100 can be secured by suturing or anchoring through the flap 510 to bone, ligaments, the plantar fascia, tissue, or other foot structures. In some embodiments, the flap 510 can be secured to the structures surrounding the implant 100 using adhesive.

In some embodiments, the flap 510 can extend from the surface of the implant 100 around the periphery of the implant 100 (as shown in FIG. 6B). In some embodiments, the flap 510 does not extend entirely around the periphery of the implant 100. In some embodiments, the flap 510 comprises a plurality of flaps. The shape and position of the flap 510 (or flaps) can be varied without limitation. In some embodiments, the flap 510 (or flaps) extends from each side of the implant 100 such that the implant 100 can be anchored in place from any side.

FIG. 6C is a diagram illustrative of an embodiment of the implant 100 that includes a reinforced ring 517 in the corners of the implant 100 for anchoring the implant 100 in place. In some embodiments, the reinforced ring 517 can include a grommet, washer, or the like. The corners can be substantially flat. A reinforced ring 517 can be included in each corner for anchoring the implant 100. The reinforced ring can include a hole extending therethrough. An anchor or suture can be inserted through the reinforced ring 517 to secure the implant 100. The anchor or suture can be attached to bone, ligaments, the plantar fascia, tissue, or other foot structures of the foot. In some embodiments, the reinforced rings 517 are positioned in other positions on the implant 100 in addition to, or as an alternative to, being positioned in the corners. In some embodiments, between one and ten or more reinforced rings 517 can be included. In some embodiments, as in the illustrated embodiment of FIG. 6C, the implant 100 includes four corners, each having a reinforced ring 517. In some embodiments, the reinforced rings 516 can be positioned to correspond with desired mounting locations. For example, in some embodiments, the reinforced rings 516 can be positioned such that the implant can be secured to the outside, bottom, or top of the first and fifth metatarsals when the implant 100 is installed in the ball of the foot via bone screws or sutures. Surgical adhesive can also be used, for example, to attach the implant to the plantar fascia. In some embodiments, the reinforced rings 516 can be positioned such that the implant can be secured to the outside, inside, bottom, top, or back of the calcaneus via bone screws or sutures. Surgical adhesive can also be used, for example, to attach the implant to the plantar fascia and/or bone.

FIG. 6D is a diagram illustrative of an embodiment of the implant 100 that includes bands 520 that can be used to secure the implant. In the illustrated embodiment of FIG. 6D, a band 520 extends from first and second opposite sides of the implant 100. However, it will be understood that the bands can be configured in a variety of ways. For example, the implant can include only one band 520 and/or multiple bands could extend from the same side, or from perpendicular sides (e.g., one band on a side of the implant 100 and another band on a top or bottoms of the implant 100, etc.). The bands 520 can comprise straps, strands, strings, wires, etc. The bands 520 can be used to secure the implant 100. In some embodiments, the bands 520 can include one more holes 522 extending there through. In some embodiments, the hole 522 can be reinforced similar to the reinforced rings 517 described above. Sutures and/or anchors can be inserted through the holes 522 to secure the implant in place. In some embodiments, the holes 522 are omitted. The bands 522 can comprise a pierceable yet durable material. Sutures and anchors can be inserted through the bands 522 to secure the implant 100.

In some embodiments, the implant 100 is configured such that the body of the implant 100 can be placed in the region to be treated and the bands 520 can extend therefrom to secure the implant 100. For example, the bands 520 can extend across the foot and be secured on both sides of the foot. As another example, the bands 520 could extend to and be secured to adjacent metatarsals for anchoring. As another example, the bands 520 can be wrapped around a metatarsal and then sewn together or anchored from above. In some embodiments, the bands 520 can be woven around the metatarsals and/or plantar fascia to secure the implant. Furthermore, the bands 520 can include any one or any combination of the exterior surface structures as described in greater detail above.

Figure 6E:
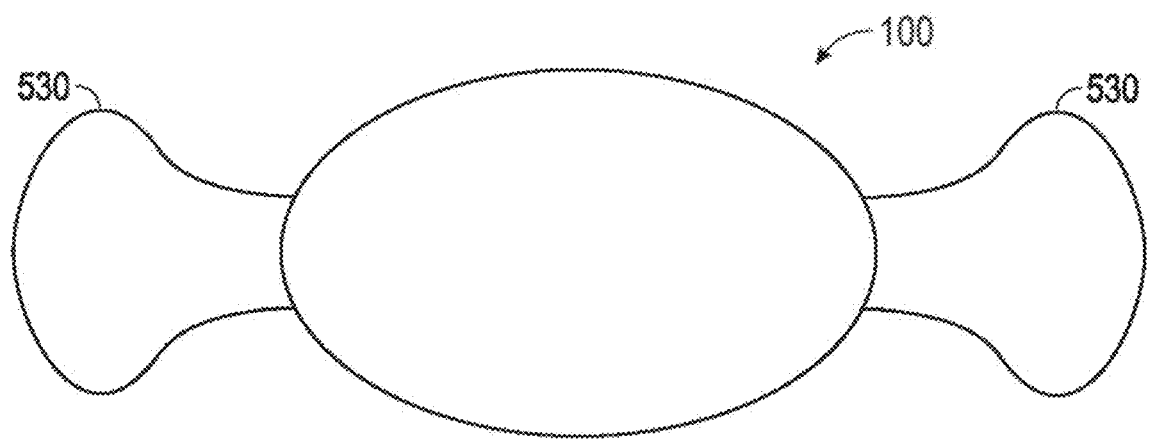
FIG. 6E is a diagram illustrative of an embodiment of an implant that includes appendages that can be used to secure the implant.

FIG. 6E is a diagram illustrative of a top-down view of an embodiment of the implant 100 that includes appendages 530 that can be used to secure the implant. In the illustrated embodiments, the appendages 530 extend from the implant 100 on opposite sides. However, it will be understood that the appendages 530 can be configured in a variety of ways. For example, the implant 100 can include only one appendage and/or multiple appendages could extend from the same side, or from perpendicular sides, etc. (e.g., one appendage 530 on a side of the implant 100 and another appendage 530 on a top or bottoms of the implant 100, etc.). The appendages 530 can be configured in size and shape to secure the implant in place. For example, the appendages 530 can be configured in size and shape to be inserted between metatarsals or between the plantar fascia to secure the implant 100. In some embodiments, the appendages 530 can be secured to foot structures with sutures, anchors, adhesives, etc. In the illustrated embodiment of FIG. 6E, the width of the appendages 530 increases on the more distal portions of the appendage 530 from the implant pad of the implant 100. In certain embodiments, the thickness of the appendage 530 can also increase at the more distal portions of the appendage 530 from the implant pad of the implant 100. In some cases, the width and/or thickness of the appendages 530 can decrease at the more distal portions of the appendage 530 from the implant pad of the implant 100.

In some embodiments, the appendages 530 can comprise cavities filled with a filler or be made of a solid material. The filler may be the same or different than the filler of the implant 100. When using a filler, the appendages 530 can be filled with the filler during surgery to customize the shape and size for the patient. The appendages 530 can be rigid or pliable. In certain cases, the appendages 530 can have a thickness that is less than the thickness of the implant pad of the implant 100. In some embodiments, the appendages 530 can have a thickness that is greater than the thickness of the implant pad of the implant 100.

In some embodiments, the appendages 530 are separated from the implant pad of the implant 100 by an impermeable barrier, such that filler cannot flow between the implant pad and the appendages 530. In some embodiments, the barrier may be permeable or semi-permeable.

In some embodiments, the appendages 530 comprise a fork shape that includes prongs. In some embodiments, the prongs may be woven around metatarsals or the plantar fascia to prevent the implant 100 from migrating. Furthermore, the appendages 530 can include any one or any combination of the exterior surface structures as described in greater detail above.

Figure 6F:
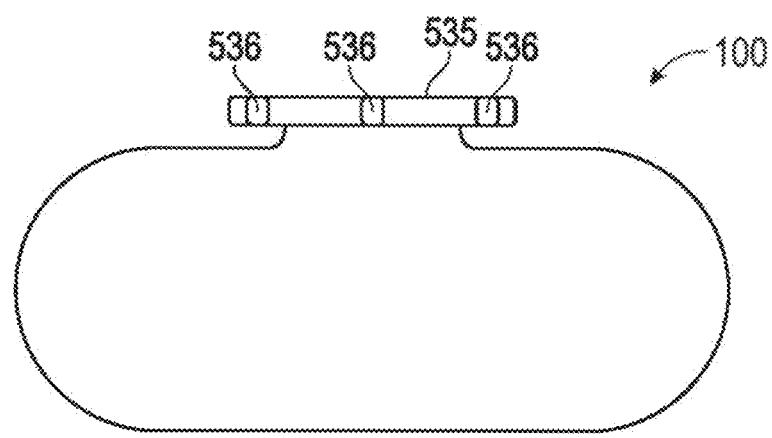
FIGS. 6F and 6G are diagrams illustrative of side and top views, respectively, of an embodiment of an implant that includes a mounting plate that can be used to secure the implant.
Figure 6G:
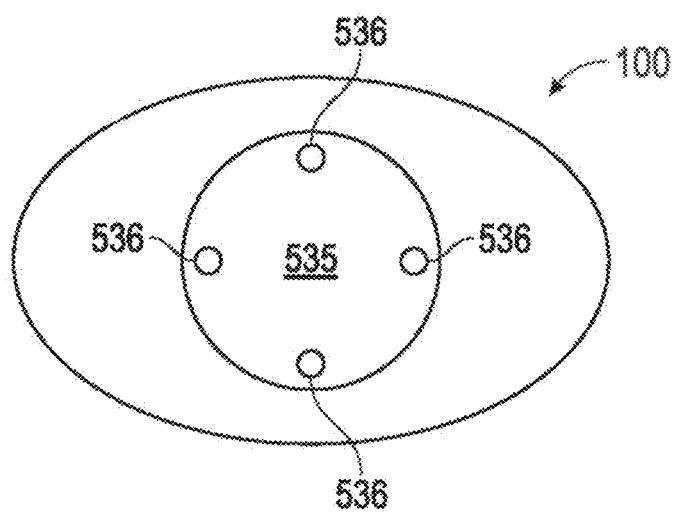

FIGS. 6F and 6G are diagrams illustrative of side and top views, respectively, of an embodiment of the implant 100 that includes a mounting plate 535 that can be used to secure the implant 100. The mounting plate 535 can comprise a rigid or a pliable material. The mounting plate 535 can be attached to the implant pad of the implant 100. In some embodiments, the mounting plat 535 is smaller than the implant pad of the implant 100.

The implant pad of the implant 100 can comprise a mushroom shape including a narrow neck attached to the mounting plate and a larger body extending therefrom. The mounting plate 535 can include one or more holes 536. In some embodiments, the holes 536 are omitted. The mounting plate 535 can be used to secure the implant 100 to structures of the foot, such as to the metatarsal corresponding to the fat pad that is to be treated, using sutures, anchors, adhesives, etc.

In the illustrated embodiment of FIGS. 6F and 6G, the mounting plate 535 is positioned on the top of the implant pad of the implant 100. Other positions for the mounting plate 535 are also possible. For example, the mounting plate 535 can be positioned on the bottom or sides of the implant pad of the implant 100. In some embodiments, the implant 100 can include multiple mounting plates 535. For example, where the implant 100 extends across multiple metatarsals, the implant can include multiple mounting plates 535 positioned to secure the implant 100 to each metatarsal.

In some embodiments, the implant 100 can be secured into a socket. For example, a socket or depression can be formed in a foot structure, such as a metatarsal. The implant 100 can be placed into the socket or depression. A cover including an opening can be placed over the implant 100 and secured around the socket or depression. A portion of the implant 100 can extend through the opening of the cover.

The implant 100 can be configured with any combination of the anchoring methods described herein. In some embodiments, the implant 100 can be configured for use with any of the anchoring methods described herein or any combination of these methods such that the implant can be secured in substantially all directions.

In some embodiments, anchors, such as bone screws or other biocompatible mechanical fastening mechanisms, can be secured to the bottom, sides, and/or top of bones, ligaments, tendons, tissues, or plantar fascia of the foot. In some embodiments, sutures can be used to secure the implant by suturing through or around the bottom, sides, and/or top of bones, ligaments, tendons, tissues, or plantar fascia of the foot. In some embodiments, the anchoring mechanisms of the implant 100 can be shaped to engage with physiological structures of the foot. For example, the anchoring mechanisms can be configured to fit between, mesh with, or otherwise engage the metatarsals, tendons, ligaments, and/or plantar fascia in a complimentary manner that resists migration of the implant 100.

Figure 7A:
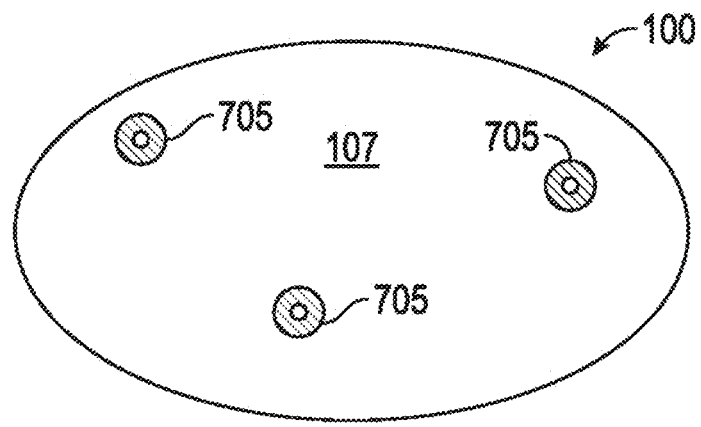
FIGS. 7A and 7B are each a diagram illustrative of an embodiment of an implant that includes ports for adjusting the amount of filler within the cavity of the implant.
Figure 7B:
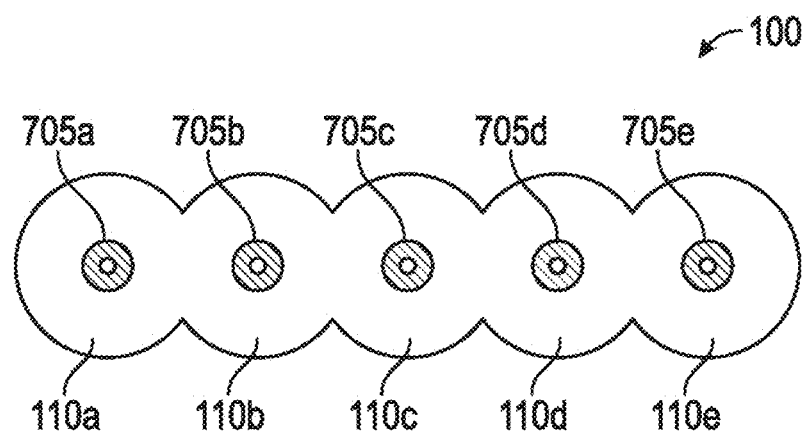

FIGS. 7A and 7B are each a diagram illustrative of an embodiment of the implant 100 that includes ports 705 for adjusting the amount of filler within the cavity 107 of the implant 100. The implant 100 can include one or more ports 705 for adjusting the mount of filler within the cavity. For example, in the embodiment illustrated in FIG. 7A, the implant 100 includes three ports 705. In the embodiment illustrated in FIG. 7A, the implant 100 includes five conjoined implant pads 110a-110e each including a port 705a-705e for filling each implant pad. In some embodiments, the ports 705 comprise valves. The valves may be one-way or two-way valves. In some embodiments, the ports 705 are positioned on the implant such that the ports are accessible after the implant 100 is installed. In some embodiments, the ports 705 are positioned on the bottom or side of the implant 100. In some embodiments, the ports 705 extend through the skin. In some embodiments, the ports 705 are positioned below the surface of the skin. The ports 705 may include a tracer that allows a doctor to locate the ports 705 even when the ports are not visible. In some embodiments, the tracer may comprise a radioactive tracer, label, or marker.

In some embodiments, the ports 705 may be used to fill the implant 100 during installation. In some embodiments, the ports 705 are used to fill or remove filler from the implant 100 after installation to adjust the implant 100. For example, in some embodiments, additional filler can be introduced through the ports 705 into the implant 100 to compensate for continued atrophy of the patient's fat pad.

As noted throughout this disclosure, the implant 100 can include any of the features described herein as well as any and all possible combinations of the those features. Furthermore, it will be understood that any of the embodiments described herein with reference to the ports can be combined with the aforementioned embodiments of the implant 100.

Example Methods for Treatment

In some embodiments, a method for treatment of fat pad atrophy using the implant 100 comprises surgically installing the implant 100 in the region of fat pad atrophy.

Figure 8:
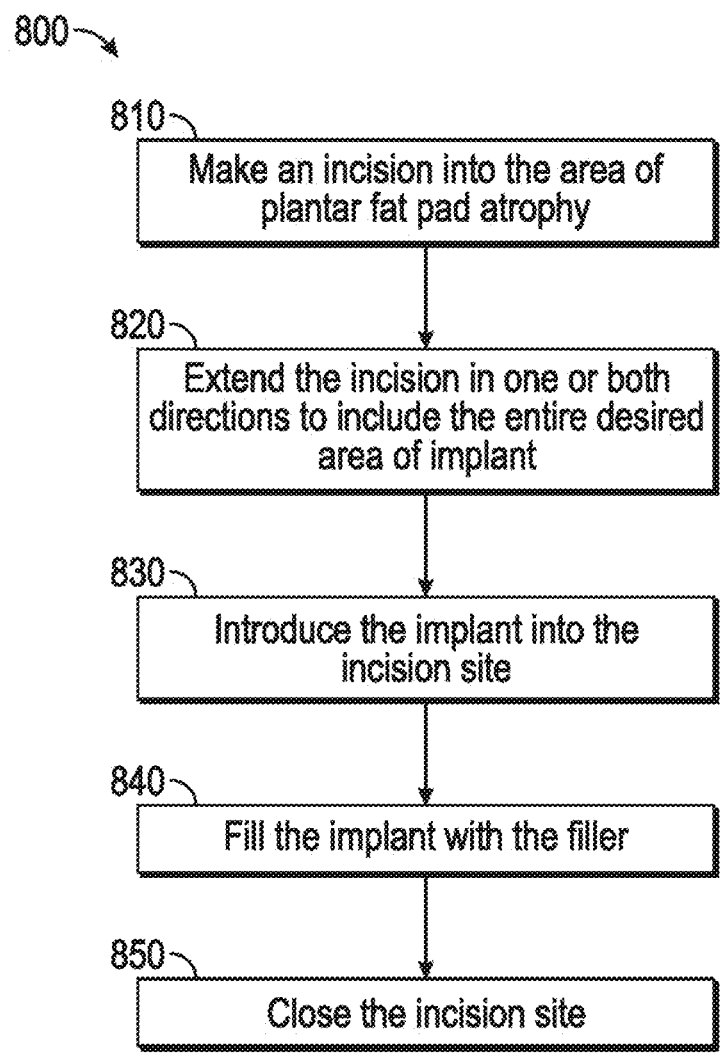
FIG. 8 is a flowchart depicting one embodiment of a method for treating fat pad atrophy using an implant.

FIG. 8 is a flowchart depicting one embodiment of a method 800 for treating fat pad atrophy using the implant 100. The illustrated blocks of the method 800 are provided by way of example and can be varied or omitted in some embodiments. Additionally, in some embodiments, the method 800 may include additional steps or blocks.

The method 800 can begin at block 810 by making an incision into the area of plantar fat pad atrophy. In some embodiments, the area of plantar fat pad atrophy can be between the sub-metatarsal heads one through five of the foot. In some instances, the implant can be inserted into all or some of this region. In some embodiments, the implant can be placed proximate to or within the subdermal layer of skin.

In some embodiments, the initial incision of block 810 can be approximately 15 mm deep. The incision can be deepened via sharp and blunt dissection to the subdermal layer. In some embodiments, the incision can also be located at the position of the third metatarsal head. In some embodiments, the incision can be made through the bottom of the foot. In some embodiments, the incision can be made above the bottom of the foot in the region where the toes extend from the foot. In some embodiments, the incision can be made on the medial or lateral side of the foot. The skin can then be separated by the overlying subdermal tissue. The skin can also be undermined outwards to the first and fifth metatarsal heads, respectively. At this point, the plantar fascial slip sub third metatarsal head can be visualized and separated from any surrounding tissue.

In some embodiments, the method 800 can continue at block 820 by extending the incision in one or both directions to include the entire desired area of implant. For example, in some embodiments, the incision is extended outwards to the first and fifth metatarsal heads, respectively. This extension can be accomplished using an approximately 5 mm deep incision. The incision can also be deepened via sharp and blunt dissection. In some embodiment, the skin can then be separated by the overlying subdermal tissue. In some embodiments, at this point, the plantar fascial slips sub first and third metatarsal heads, respectively, can be visualized and separated from any surrounding tissue.

The method 800 can continue at block 830 by introducing the implant into the incision site. The implant can be placed sterilely into the implant site, taking care not to entrap or damage any neurovascular structures. In some embodiments, a medial wing of the implant can be inserted into the implant site first, followed by a lateral wing. In some embodiments, this may be reversed. The implant can then be secured in place by the use of sutures, anchors, or adhesives connecting the implant to the surrounding soft tissue and/or metatarsals. In some embodiments, implant can be anchored to the plantar fascial slip. In some embodiments, the sutures, anchors, or adhesives can connect the medial and lateral wings of the implant to one or more plantar fascial slips both distally and proximally.

In some embodiments, the method 800 continues at block 840 by filling the implant with the filler. The implant can then be monitored to ensure that the correct level of filler has been used, and that there has been no shift in the position of the implant. The filler may be introduced through the ports of the implant. In some embodiments, the implant may be prefilled or solid (not requiring filler). At block 850, the incision site can be closed.

The surgery associated the method 800 can take place in a hospital operating room or in a doctor's office, or it can be done on an out-patient basis. The conditions and technique of the surgery will ideally be sterile and aseptic. It will be understood that fewer or more blocks can be used as desired. For example, in some embodiments, blocks 820 and 840 can be omitted.

The following example describes the steps of one embodiment of the disclosure. The following example is merely exemplary in nature and is in no way intended to limit the disclosure, its application, or uses. In this example, the surgeon will perform the following steps in inserting the implant into the patient:

1. Make a 15 mm linear incision on the plantar aspect of the foot, sub 3rd metatarsal head.
2. Deepen the incision via sharp and blunt dissection, to the subdermal layer.
3. Utilizing blunt dissection, separate the skin from the overlying subdermal tissue, taking care not to damage any neurovascular structures.
4. Undermine the skin from the third metatarsal head to first and fifth metatarsal heads, respectively, utilizing blunt dissection.
5. Visualize the plantar fascial slip sub third metatarsal head.
6. Utilizing blunt dissection, separate this slip away from any surrounding tissue.
7. Make a 5 mm incision plantar medial to the first metatarsal head, and plantar lateral to the fifth metatarsal head.
8. Deepen the incision via sharp and blunt dissection to the subdermal layer.
9. Utilizing blunt dissection, separate the skin from the overlying subdermal tissue, taking care not to damage any neurovascular structures.
10. Extend this incision until contiguous with the previously undermined tissue from step 4.
11. Visualize the plantar fascial slip sub first and fifth metatarsal heads.
12. Utilizing blunt dissection, separate this slip away from any surrounding tissue.
13. Introduce the sterile implant.
14. Utilizing blunt instrumentation, insert the medial wing of the implant, taking care not to entrap or damage any neurovascular structures, until it is visible from the medial incision.
15. Utilizing blunt instrumentation, insert the lateral wing of the implant, taking care not to entrap or damage any neurovascular structures, until it is visible from the lateral incision.
16. Ensure that the implant is situated properly on all planes.
17. Suture the anchors.
18. Suture medial wing of the device, one attachment distally, one proximally.
19. Attention is then drawn laterally to the lateral wing of the device.
20. Visualize the suture points, and the plantar fascial slip of the fifth metatarsal.
21. Suture the lateral wing of the implant, one attachment proximally, one distally.
22. Visualize implant and ensure correct placement before proceeding.
23. Draw attention to the middle of the foot and the incision, locate the plantar fascial slip to the third metatarsal.
24. Using suture points, suture both proximally and distally of the third metatarsal.
25. Evaluate position of implant, for correct placement.
26. Once correct placement ensured, fill implant with filler to the proper level (if fillable implant used)
27. Evaluate for correct level of filler as well as no shift in placement.
28. Begin closure of the subcutaneous tissues, with absorbable suture material
29. Coat the patient's skin with non-absorbable suture material.

This example is non-limiting. In some embodiments, the steps can be modified, omitted, and/or performed in a different order. In some embodiments, additional steps can also be included.

Non-Limiting Example Embodiments

Various example embodiments of the disclosure can be described in view of the following clauses:

Clause 1. A foot implant for treating fat pad atrophy, the foot implant comprising:
- a plurality of conjoined implant pads, at least two of the plurality of conjoined implant pads having a different size, each implant pad comprising
  - a non-permeable external lining formed of a plurality of materials, each material having a different resonant frequency, wherein an external surface of the external lining includes a plurality of depressions, and
  - an internal cavity enclosed by the external lining and comprising a plurality of chambers separated by a non-permeable material, wherein each chamber includes a flexible matrix, wherein walls of the flexible matrix include multiple semi-permeable layers of different materials, wherein pores in each layer are offset with respect to pores in an adjacent layer, each chamber being filled with a liquid having a higher viscosity than water; and
- a mounting area comprising a plurality of screw holes for mounting the foot implant to at least one metatarsal.

Clause 2. The foot implant of Clause 1, wherein the mounting area further comprises a first band extending from a first side of the external lining of the implant pad and a second band extending from a second side of the external lining of the implant pad, the second side opposite the first side.

Clause 3. The foot implant of Clause 2, wherein the first band is configured to be attached to a first metatarsal, and wherein the second band is configured to be attached to a second metatarsal.

Clause 4. The foot implant of any of Clauses 2-3, wherein the first and second bands are configured to secure the foot implant by interweaving with one or more metatarsals and/or one or more portions of a plantar fascia.

Clause 5. The foot implant of any of Clauses 1-4, wherein the mounting area further comprises one or more screw holes for mounting the foot implant to at least a portion of a plantar fascial slip.

Clause 6. The foot implant of any of Clauses 1-5, wherein the mounting area further comprises a surface for mounting the foot implant to at least a portion of a plantar fascial slip using a surgical adhesive.

Clause 7. A foot implant for treating fat pad atrophy, the foot implant comprising:
- an implant pad comprising:
  - a non-permeable external lining formed of a plurality of materials, each material of the plurality of materials having a different resonant frequency, wherein an external surface of the external lining is non-planar, and
  - an internal cavity enclosed by the external lining and comprising a flexible matrix, wherein walls of the flexible matrix include multiple semi-permeable layers, at least two of the multiple semi-permeable layers composed of a different material, wherein pores in a first layer are offset with respect to pores in an adjacent layer, the internal cavity further comprising a liquid having a higher viscosity than water; and
- a mounting area configured for mounting the implant pad to at least one metatarsal.

Clause 8. The foot implant of Clause 7, wherein the implant pad comprises a plurality of conjoined implant pads, each conjoined implant pad separated from each adjacent conjoined implant pad by a semi-permeable interface.

Clause 9. The foot implant of any of Clauses 7-8, wherein the mounting area comprises one or more loops extending from the external lining of the implant pad.

Clause 10. The foot implant of any of Clauses 7-9, wherein the mounting area comprises a mounting bracket attached on a side of the external lining that is proximal to a metatarsal.

Clause 11. The foot implant of any of Clauses 7-10, wherein the mounting area comprises one or more screw holes.

Clause 12. The foot implant of any of Clauses 7-11, wherein the mounting area includes a first band extending from a first side of the external lining of the implant pad and a second band extending from a second side of the external lining of the implant pad, the second side opposite the first side.

Clause 13. The foot implant of Clause 12, wherein the first band is configured to be attached to a first metatarsal, and wherein the second band is configured to be attached to a second metatarsal.

Clause 14. The foot implant of any of Clauses 12-13, wherein the first band and the second band comprise pliable arms configured to substantially anchor the foot implant by weaving with anatomical structures of a foot.

Clause 15. The foot implant of any of Clauses 7-14, wherein the mounting area comprises a first appendage on a first side of the implant pad and a second appendage on a second side of the implant pad, the second side opposite the first side, and wherein the first and second appendages are configured in size and shape to substantially anchor the foot implant in place by engaging with anatomical structures of a foot.

Clause 16. The foot implant of any of Clauses 7-15, wherein an external surface of the implant pad includes a texture that includes a multi-directional pattern.

Clause 17. The foot implant of Clause 16, wherein the multi-directional pattern comprises interconnected multi-directional ridges separated by multi-directional valleys.

Clause 18. The foot implant of any of Clauses 7-17, wherein an external surface of the implant pad includes depressions.

Clause 19. The foot implant of Clause 18, wherein the depressions are configured to receive cellular growth to anchor the foot implant in place.

Clause 20. The foot implant of any of Clauses 7-19, wherein an external surface of the implant pad includes a plurality of finger-like protrusions.

Clause 21. The foot implant of any of Clauses 7-20, wherein an external surface of the implant pad includes a plurality of non-geometric protrusions configured in size and shape to mimic a shape of fat globules.

Clause 22. An implant, the implant comprising:
- an implant pad comprising:
  - a plurality of stratified linings, each lining comprising a plurality of layered materials, wherein at least two of the plurality of layered materials have a different resonant frequency, and
- a mounting area configured for mounting the implant pad.

Clause 23. A method for the treatment of fat pad atrophy, comprising:

making an incision into a foot in a region of fat pad atrophy;
introducing an implant into the incision, the implant comprising an implant pad and a mounting area;
anchoring the implant into the foot by attaching the mounting area to structures of the foot; and
closing the incision.

Clause 24. The method of Clause 23, further comprising filling the implant pad with a filler material.

Clause 25. The method of any of Clauses 23-24, wherein said making an incision into a foot comprises making an incision into a bottom surface of the foot.

Clause 26. The method any of Clauses 23-24, wherein said making an incision into a foot comprises making an incision into the foot above the bottom of the foot and below where the toes connect to the ball of the foot.

Clause 27. The method of any of Clauses 23-26, wherein the region of fat pad atrophy is in the ball of the foot.

Clause 28. The method of any of Clauses 23-26, wherein the region of fat pad atrophy is in the heel of the foot.

Clause 29. The method of any of Clauses 23-28, wherein said making an incision into a foot comprises:
making an incision that is approximately 15 mm deep; and
deepening the incisions via sharp and blunt dissection to the subdermal layer.

Clause 30. The method of any of Clauses 23-29, further comprising visualizing and separating the fascial slip sub third metatarsal head and any surrounding tissue.

Clause 31. The method of any of Clauses 23-30, wherein said anchoring the implant into the foot comprises using bone screws to attach the implant to a metatarsal.

Clause 32. The method of any of Clauses 23-31, wherein the bone screws are attached to a lateral or medial side of a metatarsal.

Clause 33. The method of any of Clauses 23-32, wherein said anchoring the implant into the foot comprises using sutures to attach the implant to a metatarsal.

Clause 34. The method of any of Clauses 23-33, wherein said anchoring the implant into the foot comprises using sutures to attach the implant to the plantar fascia.

Clause 35. The method of any of Clauses 23-34, wherein said anchoring the implant into the foot comprises using surgical adhesive to attach the implant to a metatarsal.

Clause 36. The method of any of Clauses 23-35, wherein said anchoring the implant into the foot comprises using surgical adhesive to attach the implant to the plantar fascia.

Clause 37. The method of any of Clauses 23-36, wherein said anchoring the implant into the foot comprises:
using surgical adhesive to attach the implant to the plantar fascia; and
using bone screws to attach the implant to a metatarsal.

Clause 38. An implant, comprising:
an implant pad comprising:
a non-permeable external lining, wherein an external surface of the external lining is non-planar, and
an internal cavity enclosed by the external lining and comprising a filler material, having a higher viscosity than water.

Clause 39. The implant of Clause 38, wherein the external surface of the external lining comprises a textured surface configured to reduce migration of the implant when installed.

Clause 40. The implant of Clause 39, wherein the textured surface comprises a multi-directional pattern of interconnected multi-directional ridges separated by multi-directional valleys.

Clause 41. The implant of any of Clauses 39-40, wherein the textured surface comprises hook and loop protrusions.

Clause 42. The implant of any of Clauses 39-41, wherein the textured surface comprises finger-like protrusions.

Clause 43. The implant of any of Clauses 39-42, wherein the textured surface comprises a plurality of depression configured to receive intercellular growth.

Clause 44. The implant of any of Clauses 38-43, wherein the internal cavity further comprises a flexible matrix, and wherein walls of the flexible matrix include multiple semi-permeable layers, at least two of the multiple semi-permeable layers composed of a different material, wherein pores in a first layer are offset with respect to pores in an adjacent layer.

Clause 45. The implant any of Clauses 38-44, wherein the filler material comprises a non-Newtonian fluid.

Clause 46. The implant of Clause 45, wherein the non-Newtonian fluid is a shear thickening fluid.

Clause 47. The implant of any of Clauses 38-46, further comprising a mounting area configured for mounting the implant pad.

Clause 48. The implant of any of Clauses 47, wherein the mounting area comprises a flap.

Clause 49. The implant of Clause 48, wherein the flap includes at least one reinforced ring configured to receive a bone screw or a suture.

Clause 50. The implant of any of Clauses 48-49, wherein the flap includes a surface for anchoring the implant to a structure with adhesive.

Clause 51. The implant of any of Clause 38-50, wherein the mounting area comprises a first appendage on a first side of the implant pad and a second appendage on a second side of the implant pad, the second side opposite the first side, and wherein the first and second appendages are configured in size and shape to substantially anchor the implant in place by engaging with anatomical structures of a patient.

Clause 52. The implant of any of Clauses 38-51, wherein the mounting area comprises a first band extending from a first side of the external lining of the implant pad and a second band extending from a second side of the external lining of the implant pad, the second side opposite the first side.

Clause 53. The implant of Clause 52, wherein the first band is configured to be attached to a first metatarsal, and wherein the second band is configured to be attached to a second metatarsal.

Clause 54. The implant of any of Clauses 38-53, further comprising at least one port extending through the external lining for introducing and removing the filler material from the internal cavity.

Clause 55. An implant, the implant comprising:
an implant pad comprising a plurality of stratified linings, each lining comprising a plurality of layered materials, wherein at least two of the plurality of layered materials have a different resonant frequency.

Clause 56. The implant of Clause 55, wherein an external surface of the implant pad comprises a textured surface configured to reduce migration of the implant when installed.

Clause 57. The implant of Clause 56, wherein the textured surface comprises a multi-directional pattern of interconnected multi-directional ridges separated by multi-directional valleys.

Clause 58. The implant of any of Clauses 56-57, wherein the textured surface comprises hook and loop protrusions.

Clause 59. The implant of any of Clauses 56-57, wherein the textured surface comprises finger-like protrusions.

Clause 60. The implant of any of Clauses 56-59, wherein the textured surface comprises a plurality of depression configured to receive intercellular growth.

Clause 61. The implant of any of Clauses 55-60, further comprising a mounting area configured for mounting the implant pad.

Clause 62. The implant of any of Clauses 61, wherein the mounting area comprises a flap.

Clause 63. The implant of Clause 62, wherein the flap includes at least one reinforced ring configured to receive a bone screw or a suture.

Clause 64. The implant of any of Clauses 62-63, wherein the flap includes a surface for anchoring the implant to a structure with adhesive.

Clause 65. The implant of any of Clause 61-64, wherein the mounting area comprises a first appendage on a first side of the implant pad and a second appendage on a second side of the implant pad, the second side opposite the first side, and wherein the first and second appendages are configured in size and shape to substantially anchor the implant in place by engaging with anatomical structures of a patient.

Clause 66. The implant of any of Clauses 61-65, wherein the mounting area comprises a first band extending from a first side of the external lining of the implant pad and a second band extending from a second side of the external lining of the implant pad, the second side opposite the first side.

Clause 67. The implant of Clause 66, wherein the first band is configured to be attached to a first metatarsal, and wherein the second band is configured to be attached to a second metatarsal.

Clause 68. The implant of any of Clauses 55-67, further comprising at least one port extending through the external lining for introducing and removing the filler material from the internal cavity.

CONCLUSION

It will therefore be readily understood by those persons skilled in the art that the present disclosure is susceptible of broad utility and application. Many embodiments and adaptations of the present disclosure other than those herein described, as well as many variations, modifications and equivalent arrangements, will be apparent from or reasonably suggested by the present disclosure and the foregoing description thereof, without departing from the substance or scope of the present disclosure. Accordingly, while the present disclosure has been described herein in detail in relation to its several embodiments illustrated in the figures, it is to be understood that this disclosure is only illustrative and exemplary of the present disclosure and is made merely for purposes of providing a full and enabling disclosure of the disclosure. The foregoing disclosure is not intended to or be construed to limit the present disclosure or otherwise to exclude any such other embodiments, adaptations, variations, modifications and equivalent arrangements.

Conjunctive language such as the phrase "at least one of X, Y and Z," unless specifically stated otherwise, is otherwise understood with the context as used in general to convey that an item, term, etc. can be either X, Y or Z. Thus, such conjunctive language is not generally intended to imply that certain embodiments require at least one of X, at least one of Y and at least one of Z to each be present.

Conditional language, such as, among others, "can," "could," "might," or "can," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above detailed description using the singular or plural number can also include the plural or singular number respectively. The word "or" in reference to a list of two or more items, covers all of the following interpretations of the word: any one of the items in the list, all of the items in the list, and any combination of the items in the list. Likewise, the term "and/or" in reference to a list of two or more items, covers all of the following interpretations of the word: any one of the items in the list, all of the items in the list, and any combination of the items in the list.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the disclosure should not be taken to imply that the terminology is being re-defined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the disclosure as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties can be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A foot implant for treating fat pad atrophy, the foot implant comprising:
    an implant pad comprising:
        a non-permeable external lining formed of a plurality of materials, each material of the plurality of materials having a different resonant frequency, wherein an external surface of the external lining is non-planar, and
        an internal cavity enclosed by the external lining and comprising a flexible matrix, wherein walls of the flexible matrix include multiple semi-permeable layers, at least one layer of the multiple semi-permeable layers comprising a different material than another layer of the multiple semi-permeable layers, wherein pores in a first layer of the multiple semi-permeable layers are offset with respect to pores in an adjacent layer of the multiple semi-permeable layers, the internal cavity further comprising a liquid having a higher viscosity than water; and
    a mounting area configured for mounting the implant pad to at least one metatarsal.

2. The foot implant of claim 1, wherein the foot implant comprises a plurality of said implant pads conjoined to one another, each conjoined implant pad separated from each adjacent conjoined implant pad by a semi-permeable interface.

3. The foot implant of claim 1, wherein the mounting area comprises one or more loops extending from the external lining of the implant pad.

4. The foot implant of claim 1, wherein the mounting area comprises a mounting bracket attached on a side of the external lining that is proximal to a metatarsal.

5. The foot implant of claim 1, wherein the mounting area comprises one or more screw holes.

6. The foot implant of claim 1, wherein the mounting area includes a first band extending from a first side of the external lining of the implant pad and a second band extending from a second side of the external lining of the implant pad, the second side opposite the first side.

7. The foot implant of claim 6, wherein the first band is configured to be attached to a first metatarsal, and wherein the second band is configured to be attached to a second metatarsal.

8. The foot implant of claim 6, wherein the first band and the second band comprise pliable arms configured to substantially anchor the foot implant by weaving with anatomical structures of a foot.

9. The foot implant of claim 1, wherein the mounting area comprises a first appendage on a first side of the implant pad and a second appendage on a second side of the implant pad, the second side opposite the first side, and wherein the first and second appendages are configured in size and shape to substantially anchor the foot implant in place by engaging with anatomical structures of a foot.

10. The foot implant of claim 1, wherein the external surface of the implant pad includes a texture that includes a multi-directional pattern of interconnected multi-directional ridges separated by multi-directional valleys.

11. The foot implant of claim 1, wherein the external surface of the implant pad includes depressions.

12. The foot implant of claim 11, wherein the depressions are configured to receive cellular growth to anchor the foot implant in place.

13. The foot implant of claim 1, wherein the external surface of the implant pad includes a plurality of non-geometric protrusions configured in size and shape to mimic a shape of fat globules.

* * * * *